United States Patent
Jones et al.

(10) Patent No.: US 11,566,237 B2
(45) Date of Patent: Jan. 31, 2023

(54) SILENCING OF DUX4 BY RECOMBINANT GENE EDITING COMPLEXES

(71) Applicant: University of Massachusetts, Boston, MA (US)

(72) Inventors: Peter L. Jones, Carson City, NV (US); Charis L. Himeda, Reno, NV (US); Takako Jones, Carson City, NV (US)

(73) Assignee: University of Massachusetts, Boston, MA (US)

( * ) Notice: Subject to any disclaimer, the term of this patent is extended or adjusted under 35 U.S.C. 154(b) by 350 days.

(21) Appl. No.: 16/334,826

(22) PCT Filed: Sep. 22, 2017

(86) PCT No.: PCT/US2017/052919
§ 371 (c)(1),
(2) Date: Mar. 20, 2019

(87) PCT Pub. No.: WO2018/057863
PCT Pub. Date: Mar. 29, 2018

(65) Prior Publication Data
US 2020/0017842 A1 Jan. 16, 2020

Related U.S. Application Data

(60) Provisional application No. 62/398,801, filed on Sep. 23, 2016.

(51) Int. Cl.
| | |
|---|---|
| *C12N 15/88* | (2006.01) |
| *C12N 9/22* | (2006.01) |
| *A61P 21/00* | (2006.01) |
| *A61K 9/00* | (2006.01) |
| *C12N 15/11* | (2006.01) |
| *C12N 15/90* | (2006.01) |

(52) U.S. Cl.
CPC .............. *C12N 9/22* (2013.01); *A61K 9/0019* (2013.01); *A61P 21/00* (2018.01); *C12N 15/11* (2013.01); *C12N 15/907* (2013.01); *C12N 2310/20* (2017.05); *C12N 2750/14141* (2013.01); *C12N 2800/80* (2013.01)

(58) Field of Classification Search
CPC ....................................................... C12N 9/22
See application file for complete search history.

(56) References Cited

U.S. PATENT DOCUMENTS

2013/0288976 A1   10/2013   Van Der Maarel et al.

FOREIGN PATENT DOCUMENTS

| WO | WO-2013016352 A1 * | 1/2013 | ............ C12N 15/113 |
| WO | WO-2015006747 A2 * | 1/2015 | ............ C12N 15/111 |

OTHER PUBLICATIONS

McCullers et al. "CRISPR-Cas9 Utility in Genome Engineering." The Owl 6.1 (Apr. 12, 2016) (Year: 2016).*
Genbank Accession No. D38025. Nov. 26, 1997.
Gilbert et al., CRISPR-mediated modular RNA-guided regulation of transcription in eukaryotes. Cell. Jul. 18, 2013;154(2):442-51. doi: 10.1016/j.cell.2013.06.044. Epub Jul. 11, 2013.
Himeda et al., CRISPR/dCas9-mediated Transcriptional Inhibition Ameliorates the Epigenetic Dysregulation at D4Z4 and Represses DUX4-fl in FSH Muscular Dystrophy. Mol Ther. Mar. 2016;24(3):527-35. doi:10.1038/mt.2015.200. Epub Nov. 3, 2015.
Himeda et al., Scalpel or Straitjacket: CRISPR/Cas9 Approaches for Muscular Dystrophies. Trends Pharmacol Sci. Apr. 2016;37(4):249-251. doi:10.1016/j.tips.2016.02.001. Epub Feb. 22, 2016.
Krom et al., Intrinsic epigenetic regulation of the D4Z4 macro satellite repeat in a transgenic mouse model for FSHD. PLoS Genet. Apr. 2013;9(4):e1003415. doi: 10.1371/journal.pgen.1003415. Epub Apr. 4, 2013.
PCT/US2017/052919, Feb. 6, 2018, International Search Report and Written Opinion.
PCT/US2017/052919, Apr. 4, 2019, International Preliminary Report on Patentability.
PCT/US2017/052919, Nov. 15, 2017, Invitation to Pay Additional Fees.
Extended European Search Report for Application No. EP 17853972.2, dated Mar. 26, 2020.
Wallace et al., Developing RNAi Therapy for FSHD. Muscle and Connective Tissue. May 1, 2009;17(suppl 1):S151. doi: 10.1016/S1525-0016(16)38745-7.
Wallace et al., RNA interference inhibits DUX4-induced muscle toxicity in vivo: implications for a targeted FSHD therapy. Mol Ther. Jul. 2012;20(7):1417-23. doi: 10.1038/mt.2012.68. Epub Apr. 17, 2012.
Wang et al., Facioscapulohumeral Dystrophy. Curr Neurol Neurosci Rep. Jul. 2016;16(7):66. doi: 10.1007/s11910-016-0667-0.
Wei et al., Therapeutic RNAi for Dominant Muscle Disease. Mol Ther. J Am Soc Gene Ther. May 1, 2009;17(suppl 1):S200-S201.

* cited by examiner

Primary Examiner — Janet L Epps-Smith
Assistant Examiner — Alexander W Nicol
(74) Attorney, Agent, or Firm — Wolf, Greenfield & Sacks, P.C.

(57) ABSTRACT

The disclosure relates to methods and compositions for regulating expression of DUX4. Specifically, the disclosure provides a recombinant gene editing complex comprising: a recombinant gene editing protein; and, a nucleic acid encoding a guide RNA (gRNA) that specifically hybridizes to a target nucleic acid sequence encoding a D4Z4 macrosatellite repeat region, wherein binding of the complex to the target nucleic acid sequence results in inhibition of DUX4 gene expression. In some aspects, methods described by the disclosure are useful for treating a disease associated with aberrant DUX4 expression (e.g., facioscapulohumeral muscular dystrophy, FSHD).

13 Claims, 13 Drawing Sheets
Specification includes a Sequence Listing.

SILENCING OF DUX4 BY RECOMBINANT GENE EDITING COMPLEXES

RELATED APPLICATIONS

This application is a national stage filing under 35 U.S.C. § 371 of international application number PCT/US2017/052919, filed Sep. 22, 2017, which claims the benefit under 35 U.S.C. 119(e) of the filing date of U.S. Provisional Application Ser. No. 62/398,801, filed Sep. 23, 2016, entitled "SILENCING OF DUX4 BY RECOMBINANT GENE EDITING COMPLEXES", the entire contents of each of which are incorporated herein by reference.

GOVERNMENT SUPPORT

This invention was made with government support under grant number AR062587, awarded by the National Institutes of Health. The government has certain rights in the invention.

BACKGROUND

Facioscapulohumeral muscular dystrophy (FSHD) is caused by the aberrant expression of the DUX4 gene from an epigenetically dysregulated D4Z4 array at chromosome 4q35. This gene is generally not expressed, or expressed at very low levels, in healthy individuals. In FSHD patients, DUX4 is aberrantly expressed at higher levels in the skeletal muscles. This aberrant expression ultimately leads to muscle pathology, atrophy, and clinical weakness. Most therapies being developed target the DUX4 mRNA or protein.

Several therapeutic agents that target DUX4 mRNA or protein have been investigated for treatment of FSHD. However, effective human treatments remain needed. To date, no specific therapy exists for FSHD, and current treatments are only directed to improve behavioral symptoms. Thus, there is a general need for the development of novel compositions and methods for treating FSHD.

SUMMARY

In some aspects, the disclosure relates to compositions (e.g., recombinant gene editing complexes) useful for the treatment of diseases associated with aberrant expression of DUX4 (e.g., facioscapulohumeral muscular dystrophy, FSHD). In some embodiments, compositions (e.g., recombinant gene editing complexes) disclosed herein are useful because they transcriptionally regulate (e.g., inhibit) aberrant expression of DUX4. Without wishing to be bound by any particular theory, reduction of DUX4 expression by compositions described by the disclosure (e.g., gene editing complexes) in subjects having diseases characterized by aberrant expression of DUX4 (e.g., FSHD) is expected to result in decreased DUX4-fl expression (e.g., reduced expression of the pathogenic DUX4-fl protein), and thereby decrease disease symptomatology or reverse disease symptoms. In some embodiments, reduction of DUX4-fl expression by compositions (e.g., gene editing complexes) described by the disclosure results in reduction of certain genes that function as downstream targets of DUX4, for example TRIM43, ZSCAN4, and MBD3L2.

Accordingly, in some aspects the disclosure provides a recombinant gene editing complex comprising: a recombinant gene editing protein; and, a nucleic acid encoding a guide RNA (gRNA) that specifically hybridizes to a target nucleic acid sequence encoding a D4Z4 macrosatellite repeat region, wherein binding of the complex to the target nucleic acid sequence results in inhibition of DUX4 gene expression.

In some embodiments, the target nucleic acid sequence is located on chromosome 4 at position 4q35.

In some embodiments, the gRNA comprises or is encoded by the sequence set forth in any one of SEQ ID NOs: 1-11. In some embodiments, the gRNA specifically hybridizes to a nucleic acid sequence encoding a DUX4 promoter or exon 1 of DUX4. In some embodiments, the gRNA comprises or is encoded by the sequence set forth in any one of SEQ ID NOs: 3-8. In some embodiments, the recombinant gene editing complex comprises a plurality (e.g., 2, 3, 4, 5, 6, 7, 8, 9, 10, or more) of gRNA sequences (e.g., a plurality of a single gRNA sequence, or a plurality of different or unique gRNA sequences).

In some embodiments, the recombinant gene editing protein comprises a Cas protein, a Cfp1 protein, or a variant thereof. In some embodiments, the Cas protein is a *Streptococcus pyogenes* Cas protein (SpCas) or a *Staphylococcus aureus* Cas protein (SaCas). In some embodiments, the Cas protein is a Cas9 protein or a dead Cas9 (dCas9) protein. In some embodiments, the recombinant gene editing protein comprises the sequence set forth in SEQ ID NO: 42 or 45.

In some embodiments, the recombinant gene editing protein further comprises a transcriptional repressor domain. In some embodiments, the transcriptional repressor domain is a KRAB domain. In some embodiments, the gene editing protein comprises the sequence set forth in SEQ ID NO: 43 or 44.

In some aspects, the disclosure provides a vector comprising a nucleic acid encoding one or more components of a recombinant gene editing complex (e.g., a nucleic acid encoding a gene editing protein, a gRNA, or both) as described by the disclosure. In some embodiments, the vector is a lentiviral vector or a recombinant adeno-associated virus vector (rAAV vector).

In some aspects, the disclosure provides a host cell comprising a nucleic acid encoding one or more components of a gene editing complex as described by the disclosure.

In some aspects, the disclosure provides a composition comprising a gene editing complex (e.g., a nucleic acid encoding one or more components of a gene editing complex, or a vector comprising a nucleic acid encoding a gene editing complex) and a pharmaceutically acceptable excipient.

The disclosure relates, in part, to the discovery that, in some embodiments a gene editing complex as described by the disclosure is capable of reducing aberrant expression of DUX4. Thus in some aspects, the disclosure provides a method for inhibiting expression of DUX4 in a cell, the method comprising: contacting a cell with a nucleic acid encoding the recombinant gene editing complex as described by the disclosure, a vector as described by the disclosure, in an amount sufficient to inhibit expression of DUX4 gene in the cell.

In some embodiments, the cell comprises a D4Z4 repeat array having 11 or less repeat units. In some embodiments, the cell is obtained from a subject having or at risk of having facioscapulohumeral muscular dystrophy (FSHD). In some embodiments, the cell is in vitro or ex vivo.

In some aspects, the disclosure provides a method for treating facioscapulohumeral muscular dystrophy (FSHD) in a subject in need thereof, the method comprising: administering to the subject a therapeutically effective amount of (i) a nucleic acid encoding the recombinant gene editing complex as described by the disclosure; or, (ii) a vector as described by the disclosure.

In some embodiments, the subject is a mammal, optionally a human. In some embodiments, chromosome 4 of the subject comprises a D4Z4 repeat array having 11 or less repeat units.

In some embodiments, the administration is by injection, optionally intramuscular injection or intravenous injection.

In some embodiments, the recombinant gene editing complex is administered to muscle cells of the subject, optionally myogenic precursor satellite cells, myoblasts, myocytes, or terminally differentiated muscle cells of the subject.

In some embodiments, the recombinant gene editing complex is administered to one or more somatic cells of the subject, optionally fibroblasts or leukocytes. In some embodiments, the one or more somatic cells are isolated from the subject and reprogrammed into a myogenic lineage, for example using induced pluripotent stem cell (iPS) technology.

BRIEF DESCRIPTION OF DRAWINGS

FIG. 2A shows a schematic depiction of the D4Z4 repeat region of chromosome 10q and chromosome 4q. FIG. 2B shows data relating to the effects of using specific sgRNAs (#1-9) to target dCas9-VP64 to the FSHD locus on DUX4-fl expression.

FIG. 3A shows data relating to relative expression of DUX4-fl after targeting of dCas9-KRAB to the FSHD locus using specific sgRNAs (#1-11). FIG. 3B shows recruitment of dCas9-KRAB to the FSHD locus does not impair skeletal myocyte differentiation, as measured by relative expression level of MyHC. FIG. 3C shows recruitment of dCas9-KRAB to the FSHD locus does not repress expression of FRG1 and FRG2, as measured by relative mRNA expression.

DETAILED DESCRIPTION

Figure 1:
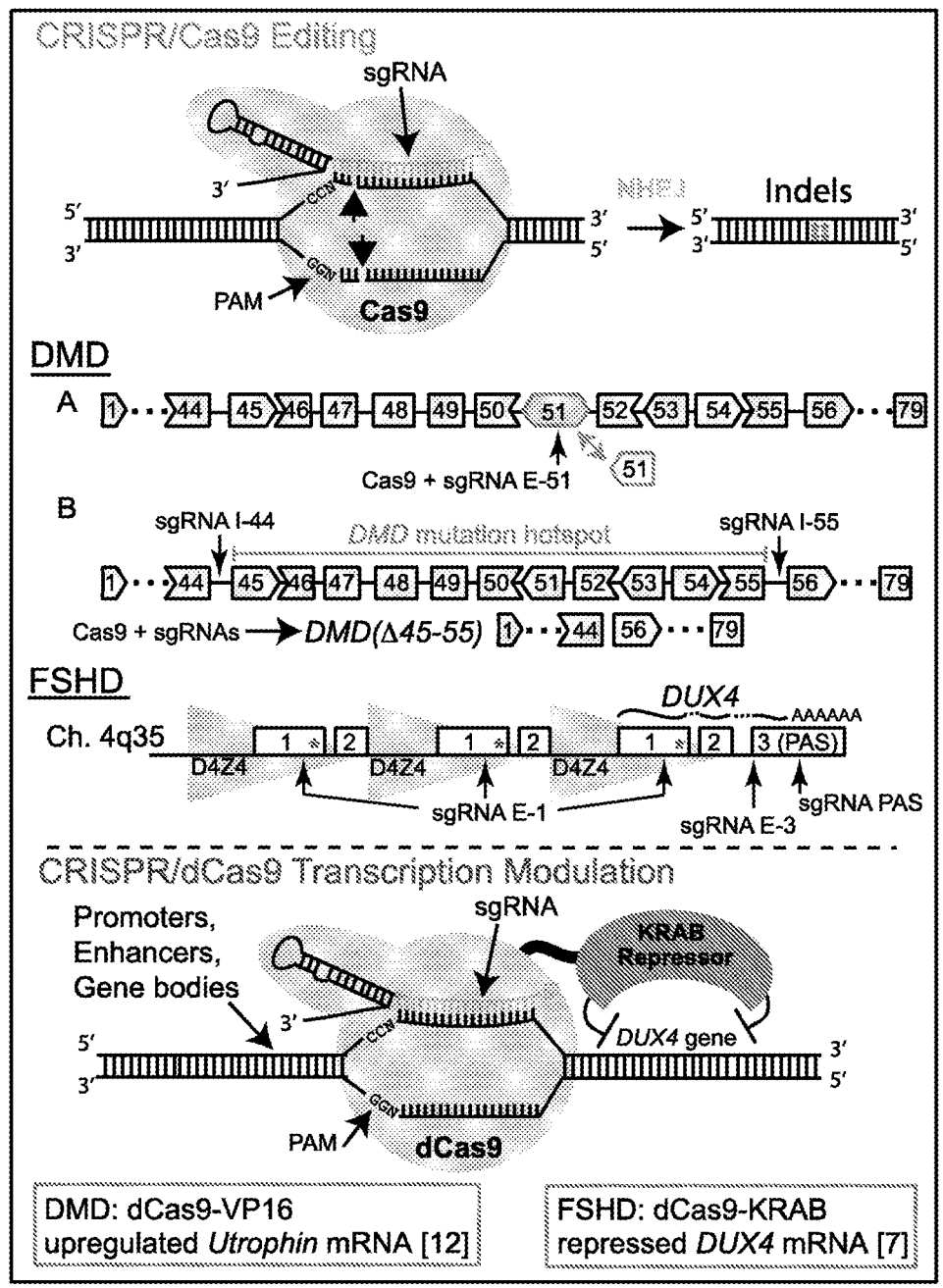
FIG. 1 shows a schematic depiction of CRISPR/Cas9 Tools for Genome Editing or Transcription Modulation in Skeletal Myocytes. (Upper panel) The Cas9 enzyme forms a complex with a sequence-specific single guide RNA (sgRNA), which guides binding to a genomic target. Cas9 cuts DNA, generating double-stranded breaks that are repaired by non-homologous end joining (NHEJ) to produce various insertions and deletions (indels) at the target sequence. (Lower panel) Catalytically inactive dCas9 is fused to transcriptional modulators (e.g., the KRAB repressor domain), to alter gene expression at defined loci. Gene editing strategies for DMD and FSHD, as described by Wojtal et al. (2016) *Am. J. Hum. Genet.* 98, 90-101, and Himeda et al. (2015) *Mol. Ther.* Doi:10.1038/mt.2015.200, respectively, are shown.

In some aspects, the disclosure relates to recombinant gene editing complexes useful for the treatment of diseases associated with aberrant expression of DUX4 (e.g., facioscapulohumeral muscular dystrophy, FSHD). The disclosure is based, in part, on the surprising discovery that recruitment of recombinant gene editing complexes to certain loci of the D4Z4 macrosatellite repeat region (e.g., at position 4q35) and/or the DUX4 gene results in decreased production of DUX4-fl, the pathogenic mRNA isoform associated with FSHD, as well as reduced expression of certain genes (e.g., TRIM43, ZSCAN4, etc.) that are downstream targets of DUX4-fl.

Facioscapulohumeral Muscular Dystrophy (FSHD)

As used herein, the term "facioscapulohumeral muscular dystrophy" or "FSHD" refers to a disease or disorder that results from transcriptional activation of the DUX4 gene. In some embodiments, activation of the DUX4 gene results in a toxic gain of function in the DUX4 gene (e.g., production of pathogenic DUX4-fl) and causes a range of symptoms including progressive skeletal muscle weakness (e.g., facial muscle weakness, shoulder weakness, etc.), hearing loss, abnormal heart rhythm, unequal weakening of biceps, triceps, deltoids and lower arm muscles, loss of strength in abdominal and/or leg muscles, a foot drop. In some embodiments, FSHD results in a subject requiring ventilatory support or wheelchair confinement.

FSHD is associated with a contraction of the D4Z4 repeat sequence at the subtelomeric region 4q35 on Chromosome 4 of the human genome. Generally, chromosome 4 of a healthy subject (e.g., a subject not having FSHD) comprises a D4Z4 repeat region having between 12 and 150 repeat units, resulting in production of an alternatively-spliced 3'-truncated DUX4 transcript (DUX4-s). Without wishing to be bound by any particular theory, the DUX4 gene of a subject having a contracted D4Z4 repeat (e.g., 11 or fewer repeat units) becomes transcriptionally activated due to the loss of repeat-mediated repression, resulting in production of pathogenic full-length DUX4 (DUX4-fl) mRNA and protein.

In some aspects, the invention relates to the discovery that recruitment of recombinant gene editing molecules to certain loci of the D4Z4 macrosatellite repeat region and/or the DUX4 gene results in decreased production of DUX4-fl protein in a subject (e.g., in a cell of a subject). As used herein, the term "D4Z4 macrosatellite repeat region" refers to a chromosomal locus comprising at least one of the following genomic features: a p13E-11 probe hybridizing sequence, a non-deleted element (NDE) sequence (e.g., a NDE sequence that functions as a transcriptional start site for a DBE-T transcript), a nucleic acid sequence encoding DUX4 (e.g., a nucleic acid sequence encoding exon 1, exon 2 and exon 3 of DUX4). In some embodiments, chromosome 4 comprises a D4Z4 macrosatellite repeat region, for example at locus 4q35.

As used herein, the term "reduced DUX4 expression" refers to a change in state of a DUX4 gene from a transcriptionally active (e.g., expressed or transcribed) state to a reduced state of transcriptional activity, for example, a transcriptionally inactive (e.g., silenced) state. For example, in some embodiments, a subject (e.g., a cell in a subject) having a transcriptionally active (e.g., expressed) DUX4 gene produces DUX4-fl; knockdown (e.g., silencing) of DUX4 expression in the subject (e.g., cell in the subject), for example by administration of a recombinant gene editing complex targeting a D4Z4 macrosatellite repeat region, leads to reduced (or inhibited) expression and production of DUX4-fl in the subject.

In some aspects, the disclosure relates to the discovery that inhibition of DUX4 expression by a recombinant gene editing complex as described by the disclosure results in reduced expression of certain genes that are downstream targets of DUX4-fl. For example, in some embodiments, inhibition of DUX4 expression by a recombinant gene editing complex as described by the disclosure results in reduced expression of TRIM43, ZSCAN4, MBD3L2, or any combination of the foregoing, as described further in the Examples section.

In some embodiments, reduction of target gene (e.g., DUX4, TRIM43, ZSCAN4) expression can be measured as expression level of the target gene (e.g., DUX4) in a sample (e.g., a cell or a subject) after treatment with a recombinant gene editing complex relative to expression level of target gene (e.g., DUX4) in the sample prior to treatment with the recombinant gene editing complex. Generally, the expression level of a target gene (e.g., DUX4) can be measured by any suitable method known in the art, for example by hybridization-based assay (e.g., RT-PCR, qRT-PCR, Northern Blot), protein-based methods (e.g., Western blot), spectroscopic methods (e.g., mass spectrometry), and cell-based methods (e.g., flow cytometry, fluorescence activated cell sorting (FACS)).

Gene Editing Molecules

The disclosure is based, in part, on the discovery of recombinant gene editing complexes that inhibit—for example, through transcriptional repression or generation of double-stranded DNA breaks-expression of the DUX4 gene.

Accordingly, in some aspects, the disclosure provides a recombinant gene editing complex comprising: a recombinant gene editing protein; and, a nucleic acid encoding a guide RNA (gRNA) that specifically hybridizes to a target nucleic acid sequence encoding a D4Z4 macrosatellite repeat region, wherein binding of the complex to the target nucleic acid sequence results in inhibition of DUX4 gene expression.

As used herein, "gene editing complex" refers to a biologically active molecule (e.g., a protein, one or more proteins, a nucleic acid, one or more nucleic acids, or any combination of the foregoing) configured for adding, disrupting or changing genomic sequences (e.g., a gene sequence), for example by causing a double stranded break (DSB) in a target DNA or inhibiting transcription of a target DNA sequence. Examples of gene editing complexes include but are not limited to Transcription Activator-like Effector Nucleases (TALENs), Zinc Finger Nucleases (ZFNs), engineered meganuclease re-engineered homing endonucleases, the CRISPR/Cas system, and meganucleases (e.g., Meganuclease I-SceI). In some embodiments, a gene editing complex comprises proteins or molecules (e.g., recombinant gene editing proteins) related to the CRISPR/Cas system, including but not limited to Cas9,Cas6, dCas9, Cpf1, CRISPR RNA (crRNA), trans-activating crRNA (tracrRNA), and variants thereof.

In some embodiments, a recombinant gene editing protein is a nuclease. As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), meganucleases (e.g., engineered meganucleases) and CRISPR-associated proteins (Cas nucleases). In some embodiments, the nuclease is a ZFN. In some embodiments, the ZFN comprises a FokI cleavage domain. In some embodiments, the ZFN comprises $Cys_2His_2$ fold group. In some embodiments, the nuclease is a TALEN. In some embodiments, the TALEN comprises a FokI cleavage domain. In some embodiments, the nuclease is a meganuclease. Examples of meganucleases include but are not limited to I-SceI, I-CreI, I-DmoI, and combinations thereof (e.g., E-Drel, DmoCre).

The term "CRISPR" refers to "clustered regularly interspaced short palindromic repeats", which are DNA loci containing short repetitions of base sequences. CRISPR loci form a portion of a prokaryotic adaptive immune system that confers resistance to foreign genetic material. Each CRISPR loci is flanked by short segments of "spacer DNA", which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease). Examples of CRISPR nucleases include, but are not limited to Cas9, dCas9, Cas6, Cpf1, and variants thereof. In some embodiments, the nuclease is Cas9. In some embodiments, the Cas9 is derived from the bacteria *Streptococcus pyogenes* (e.g., SpCas9) or *Staphylococcus aureus* (e.g., SaCas9, for example SEQ ID NO: 42). In some embodiments, a Cas protein is modified (e.g. genetically engineered) to lack nuclease activity. For example, dead Cas9 (dCas9) protein binds to a target locus but does not cleave said locus. In some embodiments, a dCas9 protein comprises the sequence set forth in SEQ ID NO: 45. In some embodiments, a Cas protein or variant thereof does not exceed the packaging capacity of a viral vector, such as a lentiviral vector or an adeno-associated virus (AAV) vector, for example as described by Ran et al. (2015) *Nature*. 520(7546); 186-91. For example, in some embodiments, a nucleic acid encoding a Cas protein is less than about 4.6 kb in length.

Aspects of the disclosure relate to the use of CRISPR-mediated regulation of transcription, such as CRISPR interference, for the reduction (e.g. silencing) of DUX4 expression. For example, in some embodiments, a catalytically dead Cas9 protein (e.g., dead Cas9, "dCas9") is fused (e.g., covalently bound) to a transcriptional regulator domain to modulate (e.g., inhibit) expression of a target gene (e.g., DUX4), as described by Qi et al. (2013) *Cell.* 152(5); 1173-1183 and Gilbert et al. (2013) *Cell.* 154(2); 442-451. In some embodiments, dCas9 comprises a sequence set forth in SEQ ID NO: 45. Without wishing to be bound by any particular theory, dCas9 (or another catalytically dead Cas protein) mediates transcriptional repression, in some embodiments, by sterically hindering the binding of transcriptional machinery (e.g., a RNA polymerase complex) to a target sequence.

In some embodiments, a CRISPR Cas protein (e.g., dCas9) is fused to a transcriptional regulator domain. As used herein a "transcriptional regulator domain" is a protein domain that catalyzes structural or chemical changes in a chromatin molecule that results in altered transcriptional activity (e.g., transcriptional activation or transcriptional repression). In some embodiments, the transcriptional regulator domain is a transcriptional repressor domain. In some embodiments, the repressive domain comprises a Kruppel associated box domain (KRAB domain). Non-limiting examples of KRAB domains include KOX1 KRAB domain, KOX8 KRAB domain, ZNF43 KRAB domain, and ZNF184 KRAB domain. In some embodiments, the KRAB domain is a KOX1 KRAB domain. In some embodiments, the gene editing protein comprises a sequence set forth in SEQ ID NO: 43 or 44. Further non-limiting examples of repressive domains include Chromo Shadow (CS) domain (e.g., CS domain of HP1α) and WRPW domain (e.g., WRPW domain of Hes1).

In some embodiments, the transcriptional regulator domain is a transcriptional activator domain. In some embodiments, the transcriptional activator domain comprises a transcriptional activation domain of Herpes simplex virus, such as VP16, or a variant thereof. Generally, a transcription factor may contain multiple activation domains, for example as described by Beerli et al. (1998) *Proc. Natl. Acad. Sci.* U.S.A. 95(25); 14628-33. Accordingly, in some embodiments, the transcriptional activator domain comprises 2, 3, 4, 5, 6, 7, 8, 9, or 10 activation domains. In some embodiments, the transcriptional activator domain is VP64, VP96, or VP160.

In some embodiments, a Cas protein is not fused to a transcriptional regulator domain, and is capable of modulating (e.g., inhibiting) gene expression via nuclease activity (e.g., DNA cleavage). Generally, Cas9 cleaves DNA at a site targeted by the guide RNA and then repaired by either non-homologous end joining (NHEJ), which is imprecise and often results in a small insertion or deletion (InDel) that disrupts the targeted sequence, or homology directed DNA repair, which allows for the insertion of a changed or new DNA sequence into the genome at a specific location. Without wishing to be bound by any particular theory, DNA cleavage by a Cas protein and subsequent repair introduce modifications into a target DNA sequence that may adversely affect (e.g., inhibit) gene expression. Accordingly, in some aspects, the disclosure relates to a gene editing complex comprising a functional nuclease and a guide RNA that hybridizes to a D4Z4 macrosatellite repeat region that is capable of reducing expression of DUX4 in a subject (e.g., a cell of a subject). In some embodiments, the guide RNA that directs the activity of the functional nuclease targets exon 3 of the DUX4 gene.

For the purpose of genome editing, the CRISPR system can be modified to combine the tracrRNA and crRNA in to a single guide RNA (sgRNA) or just (gRNA). As used herein, the terms "guide RNA", "gRNA", and "sgRNA" refer to a polynucleotide sequence that is complementary to a target sequence in a cell and associates with a Cas nuclease, thereby directing the Cas nuclease to the target sequence. In some embodiments, a gRNA (e.g., sgRNA) ranges between 1 and 30 nucleotides in length. In some embodiments, a gRNA (e.g., sgRNA) ranges between 5 and 25 nucleotides in length. In some embodiments, a gRNA (e.g., sgRNA) ranges between 10 and 22 nucleotides in length. In some embodiments, a gRNA (e.g., sgRNA) ranges between 14 and 24 nucleotides in length. In some embodiments, a Cas protein and a guide RNA (e.g., sgRNA) are expressed from the same vector. In some embodiments, a Cas protein and a guide RNA (e.g., sgRNA) are expressed from separate vectors (e.g., two or more vectors).

Typically, a guide RNA (e.g., a gRNA or sgRNA) hybridizes (e.g., binds specifically to, for example by Watson-Crick base pairing) to a target sequence and thus directs the CRISPR/Cas protein to the target sequence. In some embodiments, a guide RNA hybridizes to (e.g., targets) a nucleic acid sequence encoding a D4Z4 macrosatellite repeat region or a nucleic acid sequence encoding DUX4 gene. In some embodiments, the gRNA hybridizes to a p13E-11 sequence or a NDE sequence. In some embodiments, the gRNA hybridizes to exon 1, exon 2 or exon 3 of a DUX4 gene. In some embodiments, the gRNA comprises or is encoded by the sequence set forth in any one of SEQ ID NOs: 1-11, for example as described in Table 1.

Methods of Treatment

In some aspects, the disclosure provides methods for treating a subject having facioscapulohumeral muscular dystrophy (FSHD). For example, transcriptional activation of the DUX4 gene may lead to FSHD in a subject. As used herein, a "subject" is interchangeable with a "subject in need thereof", both of which may refer to a subject having FSHD, or a subject having an increased risk of developing such a disorder relative to the population at large. For example, in some embodiments, a subject has a D4Z4 array comprising 11 or fewer repeat units at chromosome 4q35 but does not exhibit signs or symptoms of FSHD. A subject in need thereof may be a subject having a transcriptionally active DUX4 gene (e.g., a subject expressing DUX4-fl protein). A subject can be a human, non-human primate, rat, mouse, cat, dog, or other mammal.

As used herein, the terms "treatment", "treating", and "therapy" refer to therapeutic treatment and prophylactic or preventative manipulations. The terms further include ameliorating existing symptoms, preventing additional symptoms, ameliorating or preventing the underlying causes of symptoms, preventing or reversing causes of symptoms, for example, symptoms associated with FSHD. Thus, the terms denote that a beneficial result has been conferred on a subject having FSHD, or with the potential to develop such a disorder. Furthermore, the term "treatment" is defined as the application or administration of an agent (e.g., therapeutic agent or a therapeutic composition) to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease.

Therapeutic agents or therapeutic compositions may include a compound in a pharmaceutically acceptable form that prevents and/or reduces the symptoms of a particular disease (e.g., FSHD). For example a therapeutic composition may be a pharmaceutical composition that prevents and/or reduces the symptoms of FSHD. In some embodiments, the disclosure provides a composition (e.g., a therapeutic composition) comprising a gene editing complex as described by the disclosure or a vector as described by the disclosure. In some embodiments, the composition further comprises a pharmaceutically acceptable excipient. It is contemplated that the therapeutic composition of the present invention will be provided in any suitable form. The form of the therapeutic composition will depend on a number of factors, including the mode of administration as described herein. The therapeutic composition may contain diluents, adjuvants and excipients, among other ingredients as described herein.

In some aspects, the disclosure provides a method for inhibiting (e.g., silencing) a transcriptionally active DUX4 gene in a cell, the method comprising: delivering to the cell an effective amount of gene editing complex, wherein the gene editing complex reduces DUX4 expression in the cell.

The cell containing an effective amount of a gene editing complex can be any cell that has a transcriptionally active DUX4 gene. For example, the cell can be a muscle cell (e.g., a myoblast, myocyte, or terminally differentiated muscle cell).

A cell having a transcriptionally active DUX4 gene can also comprise a contraction of a D4Z4 repeat array at chromosome 4q35 of the DUX4 gene. The number of repeat units in the array can vary. In some embodiments, the number of repeat units in the contraction is 11 or fewer (e.g., 11, 10, 9, 8, 7, 6, 5, 4, 3, 2, 1, or 0) repeat units. In some embodiments, the cell is in vitro or ex vivo.

In some aspects, gene editing complexes described by the disclosure are useful for the production of modified cells, such as ex vivo modified cells. As used herein, "ex vivo modified cell" refers to a cell (e.g., a mammalian cell) that is removed from a subject, genetically modified (e.g., transfected or transduced with exogenous nucleic acids, or genetically reprogrammed), cultured or expanded, and optionally, returned to a subject (e.g., either the same subject, or a different subject). Generally, ex vivo modified cells are useful for autologous cell therapy, or allogeneic cell therapy. For example, cells may be removed from a subject having a disease associated with a particular genetic defect (e.g., FSHD), transfected with a gene editing complex that corrects the genetic defect (e.g. reduces expression of DUX4), and reintroduced into the subject. In another non-limiting example, cells are removed from a subject, genetically reprogrammed (e.g., dedifferentiated or transdifferentiated into muscle cells), expanded, and reintroduced into the subject. In some embodiments, ex vivo modified cells produced by transfection with a nucleic acid as described by the disclosure have an improved safety profile compared to ex vivo cells produced by currently available gene therapy vectors.

Pharmaceutical Compositions

In some aspects, the disclosure relates to pharmaceutical compositions comprising a gene editing complex. In some embodiments, the composition comprises gene editing complex and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Pharmaceutical compositions can be prepared as described below. The active ingredients may be admixed or compounded with any conventional, pharmaceutically acceptable carrier or excipient. The compositions may be sterile.

Typically, pharmaceutical compositions are formulated for delivering an effective amount of an agent (e.g., gene editing complex). In general, an "effective amount" of an active agent refers to an amount sufficient to elicit the desired biological response (e.g., transcriptional repression, such as silencing or inhibition, of the active DUX4 gene). An effective amount of an agent may vary depending on such factors as the desired biological endpoint, the pharmacokinetics of the compound, the disease being treated (e.g., FSHD), the mode of administration, and the patient.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed and which is inert with respect to the active agent may be utilized for preparing and administering the pharmaceutical compositions of the present disclosure. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the disclosure, will experience no difficulty in determining suitable and appropriate vehicles, excipients and carriers or in compounding the active ingredients therewith to form the pharmaceutical compositions of the disclosure.

An effective amount, also referred to as a therapeutically effective amount, of a compound (for example, a gene editing complex or vector as described by the disclosure) is an amount sufficient to ameliorate at least one adverse effect associated with activation (e.g., transcriptional activation), or increased expression, of the gene in a cell or in an individual in need of such modulation. In some embodiments, an effective amount is an amount sufficient to inhibit (e.g., transcriptionally repress) DUX4 gene in a cell or in an individual in need of DUX4 inhibition. The therapeutically effective amount to be included in pharmaceutical compositions depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg. In the case of viral vectors, an amount of active agent can be included in each dosage form to provide between about $10^{10}$, $10^{11}$, $10^{12}$, $10^{13}$, $10^{14}$, or $10^{15}$ genome copies per subject. One of ordinary skill in the art would be able to determine empirically an appropriate therapeutically effective amount.

Combined with the teachings provided herein, by choosing among the various active compounds and weighing factors such as potency, relative bioavailability, patient body weight, severity of adverse side-effects and selected mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

In some cases, compounds of the disclosure are prepared in a colloidal dispersion system. Colloidal dispersion systems include lipid-based systems including oil-in-water emulsions, micelles, mixed micelles, and liposomes. In some embodiments, a colloidal system of the disclosure is a liposome. Liposomes are artificial membrane vessels which are useful as a delivery vector in vivo or in vitro. It has been shown that large unilamellar vesicles (LUVs), which range in size from 0.2-4.0 µm can encapsulate large macromolecules. RNA, DNA and intact virions can be encapsulated within the aqueous interior and be delivered to cells in a biologically active form. Fraley et al. (1981) Trends Biochem Sci 6:77.

Liposomes may be targeted to a particular tissue by coupling the liposome to a specific ligand such as a monoclonal antibody, sugar, glycolipid, or protein. Ligands which may be useful for targeting a liposome to, for example, an smooth muscle cell include, but are not limited to: intact or fragments of molecules which interact with smooth muscle cell specific receptors and molecules, such as antibodies, which interact with the cell surface markers of cancer cells. Such ligands may easily be identified by binding assays well known to those of skill in the art. In still other embodiments, the liposome may be targeted to a tissue by coupling it to an antibody known in the art.

Lipid formulations for transfection are commercially available from QIAGEN, for example, as EFFECTENE™ (a non-liposomal lipid with a special DNA condensing enhancer) and SUPERFECT™ (a novel acting dendrimeric technology).

Liposomes are commercially available from Gibco BRL, for example, as LIPOFECTIN™ and LIPOFECTACE™, which are formed of cationic lipids such as N-[1-(2, 3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) Trends Biotechnol 3:235-241.

Certain cationic lipids, including in particular N-[1-(2, 3 dioleoyloxy)-propyl]-N,N,N-trimethylammonium methylsulfate (DOTAP), may be advantageous when combined with the gene editing complexes and vectors of the disclosure.

In some aspects of the disclosure, the use of compaction agents may also be desirable. Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, e.g., to deliver a gene editing complex or a vector as described by the disclosure in a form that is more efficiently taken up by the cell or, in combination with one or more of the above-described carriers.

Other exemplary compositions that can be used to facilitate uptake of a gene editing complex or vector as described by the disclosure include calcium phosphate and other chemical mediators of intracellular transport, microinjection compositions, electroporation and homologous recombination compositions (e.g., for integrating a nucleic acid into a preselected location within the target cell chromosome).

The compounds may be administered alone (e.g., in saline or buffer) or using any delivery vehicle known in the art. For instance the following delivery vehicles have been described: cochleates; Emulsomes; ISCOMs; liposomes; live bacterial vectors (e.g., *Salmonella, Escherichia coli, Bacillus Calmette-Guérin, Shigella, Lactobacillus*); live viral vectors (e.g., Vaccinia, adenovirus, Herpes Simplex, Lentiviral); microspheres; nucleic acid vaccines; polymers (e.g., carboxymethylcellulose, chitosan); polymer rings; proteosomes; sodium fluoride; transgenic plants; virosomes; and, virus-like particles. In some embodiments, gene editing complexes described by the disclosure are delivered by lentiviral vector or recombinant adeno-associated virus (rAAV) vector.

The formulations of the disclosure are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In addition to the formulations described herein, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) Science 249:1527-1533, which is incorporated herein by reference.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Modes of Administration

The pharmaceutical compositions of the present disclosure preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally.

In some embodiments, a therapeutically effective amount of a gene editing complex or vector as described by the disclosure is delivered to a target tissue or a target cell. In some embodiments, DUX4 (e.g., DUX4-fl) is expressed in muscle cells of a subject having FSHD. Thus, in some embodiments, an effective amount of gene editing complex or vector is delivered to the muscle cells of a subject. In some embodiments, the muscle cells are myoblasts. In some embodiments, the muscle cells are terminally differentiated muscle cells. Examples of differentiated muscle cells include myocytes and myotubes.

The pharmaceutical compositions containing gene editing complex or vector, and/or other compounds can be administered by any suitable route for administering medications. A variety of administration routes are available. The particular mode selected will depend, of course, upon the particular agent or agents selected, the particular condition being treated, and the dosage required for therapeutic efficacy. The methods of this disclosure, generally speaking, may be practiced using any mode of administration that is medically acceptable, meaning any mode that produces therapeutic effect without causing clinically unacceptable adverse effects. Various modes of administration are discussed herein. For use in therapy, an effective amount of the gene editing complex or vector, and/or other therapeutic agent can be administered to a subject by any mode that delivers the agent to the desired surface, e.g., systemic, intramuscular, etc. In some embodiments, the gene editing complex or vector as described by the disclosure is administered to a subject via intramuscular (IM) injection.

However, it should be appreciated that administering the pharmaceutical composition of the present disclosure may be accomplished by any means known to the skilled artisan. Additional routes of administration include but are not limited to oral, parenteral, intravenous, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In some embodiments, a gene editing complex (e.g., a nucleic acid encoding one or more components of a gene editing complex) can be delivered to the cells via an expression vector engineered to express the gene editing complex. An expression vector is one into which a desired sequence may be inserted, e.g., by restriction and ligation, such that it is operably joined to regulatory sequences and may be expressed as an RNA transcript. An expression vector typically contains an insert that is a coding sequence for a protein (e.g., gene editing protein, such as a CRISPR/Cas protein) or for a polynucleotide, such as guide RNA (gRNA, sgRNA, etc.). Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays or fluorescent proteins, etc.

As used herein, a coding sequence (e.g., protein coding sequence, miRNA sequence, shRNA sequence) and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence may encode an miRNA, shRNA or siRNA.

The precise nature of the regulatory sequences needed for gene expression may vary between species or cell types, but shall in general include, as necessary, 5' non-transcribed and 5' non-translated sequences involved with the initiation of transcription and translation, respectively, such as a TATA box, capping sequence, CAAT sequence, and the like. Such 5' non-transcribed regulatory sequences will include a promoter region that includes a promoter sequence for transcriptional control of the operably joined gene. However, in some embodiments, a vector does not include a promoter sequence. Regulatory sequences may also include enhancer sequences, upstream activator sequences, internal ribosomal entry sites (IRES), and/or self-processing peptide sequences (e.g., 2A peptide), as desired. The vectors of the disclosure may optionally include 5' leader or signal sequences.

In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses, a modified retrovirus, a nonreplicating retrovirus, a replication defective Semliki Forest virus, canarypox virus and highly attenuated vaccinia virus derivative, non-replicative vaccinia virus, replicative vaccinia virus, Venzuelan equine encephalitis virus, Sindbis virus, lentiviral vectors and Ty virus-like particle.

Another virus useful for certain applications is the adeno-associated virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Generally, a recombinant AAV vector (rAAV) comprises, at a minimum, a transgene coding sequence (e.g., a nucleic acid sequence encoding a gene editing protein, such as a Cas protein, or a gRNA) and its associated regulatory sequence flanked by two AAV inverted terminal repeat (ITR) sequences. Examples of regulatory sequences include promoters (e.g., constitutive promoters, inducible promoters, tissue-specific promoters), enhancer sequences, etc. In some embodiments, the ITR sequences are AAV1, AAV2, AAV5, AAV6, AAV7, AAV8, or AAV9 ITR sequences, or variants thereof.

In some embodiments, an rAAV vector comprising a nucleic acid encoding all or part of a gene editing complex (e.g., a nucleic acid sequence encoding a gene editing protein, a gRNA, or both) is packaged into a recombinant AAV (rAAV). Typically, an AAV vector is packaged into viral particles by one or more AAV capsid proteins. The AAV capsid is an important element in determining these tissue-specific targeting capabilities. Thus, an rAAV having a capsid appropriate for the tissue being targeted can be selected. In some embodiments, the capsid protein has a serotype selected from AAV2, AAV3, AAV5, AAV6, AAV6.2, AAV7, AAV8, AAV9, AAVrh.8, AAVrh.10, AAVrh.39, and AAVrh.43. In some embodiments, the rAAV comprises a capsid protein that targets muscle cells.

In general, other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (e.g., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Clifton, N.J. (1991). In some embodiments, gene editing complex (e.g., a nucleic acid sequence encoding a gene editing protein, a gRNA, or both) is delivered to a cell (e.g. a cell of a subject) by a lentiviral vector.

Various techniques may be employed for introducing nucleic acid molecules of the disclosure into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FectoFly™ transfection reagents for insect cells by Polyplus Transfection, Polyethylenimine "Max" by Polysciences, Inc., Unique, Non-Viral Transfection Tool by Cosmo Bio Co., Ltd., Lipofectamine™ LTX Transfection Reagent by Invitrogen, SatisFection™ Transfection Reagent by Stratagene, Lipofectamine™ Transfection Reagent by Invitrogen, FuGENE® HD Transfection Reagent by Roche Applied Science, GMP compliant in vivo-jetPEI™ transfection reagent by Polyplus Transfection, and Insect GeneJuice® Transfection Reagent by Novagen.

EXAMPLES

Example 1

Materials and Methods

Plasmids and Antibodies.

The following plasmids were used in this example: pHAGE EF1-dCas9-VP64 (Addgene plasmid #50918), pHAGE EF1-dCas9-KRAB (Addgene plasmid #50919), pLKO.1-puro U6 sgRNA BfuAI stuffer (Addgene plasmid #50920), pHRdSV40-dCas9-10xGCN4-v4-P2A-BFP (Addgene plasmid #60903), and pHRdSV40-scFv-GCN4-sfGFP-VP64-GB1-NLS (Addgene plasmid #60904), pHR-scFv-GCN4-sfGFP-GB1-NLS-dWPRE (Addgene plasmid #60906).

ChIP-grade antibodies used in this example include: α-KAP1(ab3831), α-HP1α (ab77256), α-HP1β (ab10811), α-histone H3 (ab1791), α-histone H3K27acetyl (ab4729), and α-RNA Polymerase II CTD phosphor S2 (ab5095).

Other antibodies used for ChIP were α-HA high affinity (clone 3F10) and normal mouse IgG (sc-2025).

sgRNA Design and Plasmid Construction.

Figure 2A:
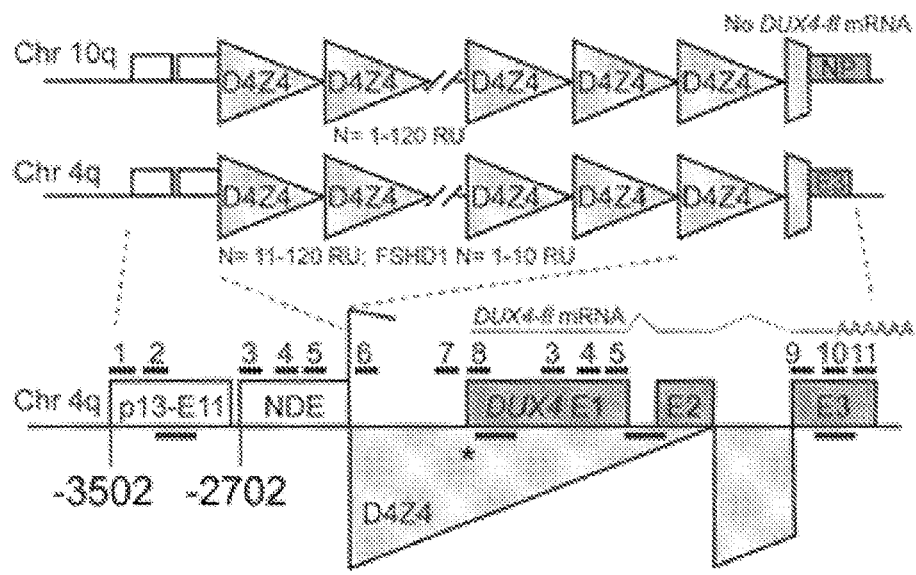
FIGS. 2A-2B show identification of single guide RNAs (sgRNAs) that target the D4Z4 region and affect expression of DUX4.

An sgRNA design tool was used to identify high-scoring candidate sgRNAs to four target regions within and flanking the D4Z4 repeat array (FIG. 2A; Table 1). Predicted off-target matches were determined by BLASTing each sequence against the human genomic database (Table 1). High-scoring, non-overlapping candidates with the fewest CpGs and off target matches (four to five sgRNAs for each target region) were cloned individually into BfuAI sites in the pLKO.1-puro U6 sgRNA BfuAI stuffer plasmid and sequence-verified.

Cell Culture, Transient Transfections, and Lentiviral Infections.

Myogenic cultures derived from biceps muscle of an FSHD1 patient (17Abic) were used in this example. Patient 17A has two permissive 4qA alleles (~5 repeat units on a contracted 4A161 allele; ~26 repeat units on the non-contracted 4A-L161 allele; each 10 q allele has ~37 repeat units). 17Abic myoblasts were grown in Ham's F-10 medium supplemented with 20% FBS (Hyclone), 0.5% chick embryo extract, 1% antibiotics and antimycotics, and 1.2 mmol/l CaCl2. 293 T packaging cells were grown in DMEM+10% FBS+0.1% penicillin-streptavidin. At ~80% confluency, 293 T cells were transfected with lentiviral packaging plasmid (pCMV-dR8.91), envelope plasmid (VSV-G), and sgRNA expression plasmid using the TransIT-LT1 transfection reagent (Mirus). Lentiviral supernatants were harvested at 11-hour intervals from 72-108 hours post-transfection. At ~70-80% confluency, 17Abic myoblasts were subjected to four serial infections. Briefly, lentiviral supernatants+8 µg/ml polybrene were added to myoblasts and the plates were incubated for 15 minutes at 37° C., then wrapped well with parafilm before centrifuging for 30 minutes at 1,100 g (32° C.). Following centrifugation, the viral supernatants were replaced with growth medium and cells were allowed to recover for ~8 hours prior to the next round of infection. Following the last round of infection, cells were switched to differentiation medium (DM) (DMEM/F-12 medium (1:1, Hyclone) plus 2% horse serum (Lonza)) for ~40-48 hours prior to harvesting.

qRT-PCR.

Total RNAs were extracted using TRIzol (Invitrogen) and purified using the RNeasy Mini kit (Qiagen) after on-column DNase I digestion. Total RNA (2 µg) was used for cDNA synthesis using Superscript III Reverse Transcriptase (Invitrogen), and 200 ng of cDNA were used for qPCR analysis. Oligonucleotide primer sequences are provided in Table 2.

ChIP.

ChIP assays were performed with lentiviral-infected 17Abic differentiated myocytes using the Fast ChIP method. Cells were fixed in 1% formaldehyde in DMEM for 10 minutes and dounced 10× prior to sonication. Cells were sonicated for 12 rounds of 15-second pulses at 65% power output on a Branson Sonifier 450 (VWR Scientific) to shear the DNA to a ladder of ~200-800 bp, and efficiency of shearing was verified by agarose gel electrophoresis. Chromatin was immunoprecipitated using 2 µg of specific antibodies or normal IgG. SYBR green quantitative PCR assays were performed for 40 cycles of: 94° C. for 15 seconds, 55° C. for 30 seconds, and 72° C. for 30 seconds. PCR products were analyzed on a 1.5% agarose gel to verify correct size of products and specificity of primer annealing. Oligonucleotide primer sequences are provided in Table 2.

Example 2

CRISPR/Cas9 Approaches for Fascioscapulohumeral Muscular Dystrophy (FSHD)

Recruitment of dCas9 and VP64 to the DUX4 Promoter or exon 1 Activates DUX4 fl in FSHD myocytes To search for potential FSHD therapeutic targets in vivo, the CRISPR/dCas9 system was used to test several candidate regions in or flanking the 4q35 D4Z4/DUX4 locus for the ability to modulate gene expression in the D4Z4 array. Polyadenylated DUX4 fl mRNA levels in FSHD1 myocytes were used as a read-out for gene expression which is specifically derived from the contracted 4q35 D4Z4 array. When targeted by small guide RNAs (sgRNAs), dCas9 transcriptional effector platforms are effective in modulating endogenous gene expression levels in mammalian cells. In this example, the SunTag system was used, which involves the dual activity of two constructs: (i) dCas9 fused to 10 copies of the GCN4 peptide and (ii) GCN4 antibody fused to the VP64 activator. The dCas9 fused directly to VP64 generally requires multiple, non-overlapping sgRNAs to achieve strong activation of gene expression. In contrast, the SunTag system allows recruitment of multiple VP64 domains to a single dCas9, resulting in robust gene activation with only a single sgRNA. Myogenic cells from an FSHD1 patient (17Abic), which express consistent and relatively high levels of DUX4 fl when terminally differentiated, were used in this example.

Single guide RNAs (sgRNAs) targeting two candidate regions upstream of the D4Z4 repeat (FIG. 2A) were produced: the NDE (non-deleted element retained in FSHD patients) sequence and p13-E11, a region distinct in the genome that is used to identify D4Z4 arrays specific to chromosomes 4q35 and 10q26. Within D4Z4, sgRNAs targeting the promoter, exon 1, and exon 3 of DUX4 were produced. In addition to forming a macrosatellite repeat, each D4Z4 repeat unit also contains repetitive sequences, and part of the DUX4 exon 1 is duplicated in the NDE, which lies proximal to the array. Thus, three sgRNAs (#3-5) target both the NDE and DUX4 exon 1. In addition, sgRNA #6 targets DUX4 intron 2 as well as the DUX4 promoter. For each target region, four to five sgRNAs were tested for the ability to recruit dCas9-VP64-HA, as assessed by chromatin immunoprecipitation (ChIP) using HA antibodies. At least two sgRNAs for each region (p13-E11, DUX4 promoter, DUX4 exon 1/NDE, and DUX4 exon 3) demonstrated correct targeting of dCas9-VP64-HA (Table 1).

Figure 2B:
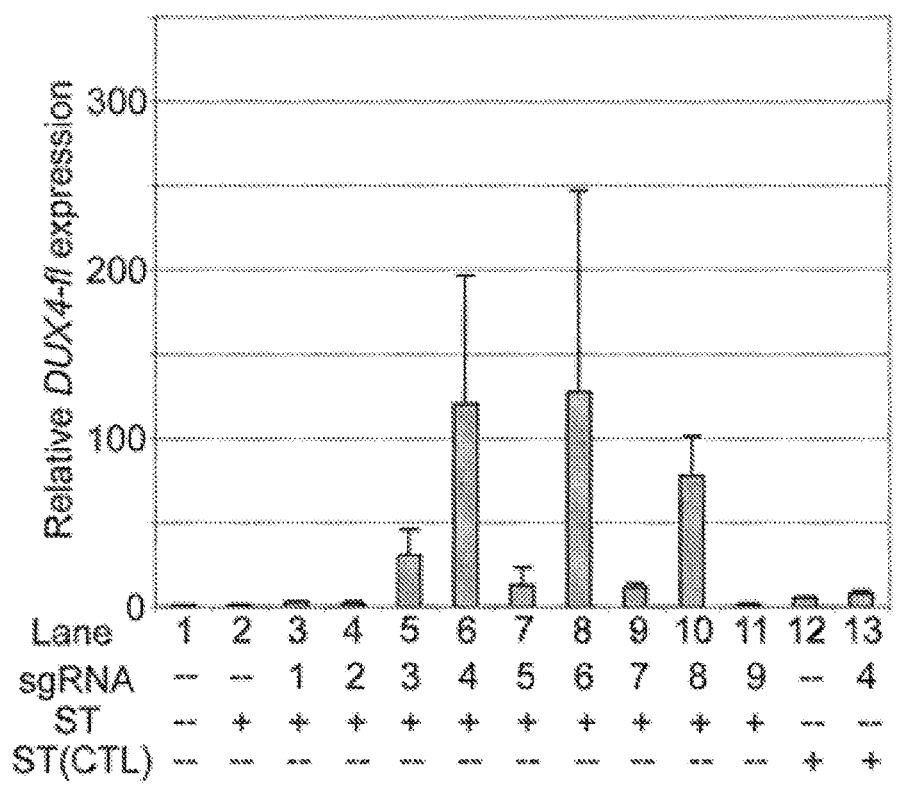

Primary myoblasts were transfected (infected) by four serial rounds of viral exposure with centrifugation. After the final round of infection, the cells were induced to differentiate and harvested 48 hours later for analysis of DUX4 fl expression by quantitative reverse transcriptase polymerase chain reaction (qRT-PCR). Expression of the SunTag system alone had no effect on DUX4 fl mRNA levels in FSHD myocytes (FIG. 2B, lane 2) Likewise, recruitment of VP64 to the p13-E11 region or to exon 3 of DUX4 had little effect on DUX4 fl expression (FIG. 2B, lanes 3, 4, and 11). In contrast to this, VP64 recruitment to the DUX4 promoter or exon 1/NDE yielded robust activation of DUX4 fl in FSHD myocytes (FIG. 2B, lanes 5-10). Recruitment to the DUX4 promoter, directly upstream of exon 1, strongly activated DUX4-fl. When guided by sgRNAs #3-5, the transcriptional effector is likely mediating its effects from DUX4 exon 1, and for simplicity, we will refer to these sgRNAs as targeting DUX4 exon 1. Although targeting by single sgRNAs proved sufficient for transcriptional activation, the functional capacity of sgRNAs targeting the same region was variable (e.g., ~120-fold activation with sgRNA #4 versus~13-fold activation with sgRNA #5) (FIG. 2B). It was observed that when dCas9 lacking a transcriptional effector domain was recruited to DUX4 exon 1, it did not activate DUX4 fl expression (FIG. 2B, lanes 12-13).

Recruitment of dCas9-KRAB to the DUX4 Promoter or exon 1 represses DUX4-fl in FSHD myocytes Reducing the aberrant expression of DUX4-fl in FSHD by returning the chromatin at the disease locus to a nonpathogenic, repressed state is a viable avenue of therapy. Whether DUX4-fl expression could be reduced in FSHD myocytes using a dCas9-KRAB repressor was examined. When guided by multiple sgRNAs, dCas9-KRAB has proven effective in reducing target gene expression in mammalian cells. Since dCas9-mediated recruitment of VP64 to the DUX4 promoter or exon 1 strongly activated DUX4-fl expression, these regions were selected as candidates for therapeutic targeting with dCas9-KRAB. Four serial coinfections of FSHD myogenic cultures were carried out. Cells were infected with various combinations of lentiviral supernatants expressing either dCas9-KRAB or individual sgRNAs targeting the candidate regions. After the final round of infection, the cells were induced to differentiate and harvested~40 hours later for analysis of DUX4-fl expression by qRT-PCR.

Figure 3A:
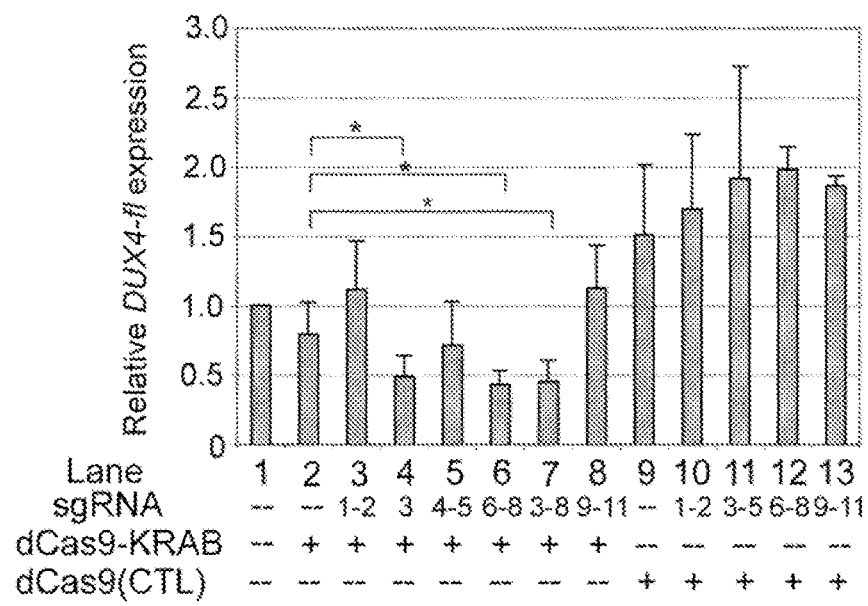
FIGS. 3A-3C show recruitment of dCas9-KRAB to the DUX4 promoter or exon 1 represses DUX4-fl in FSHD.

Expression of the dCas9-KRAB repressor alone had little effect on DUX4-fl levels (FIG. 3A, lane 2). Consistent with results observed using the SunTag activator system, targeting dCas9-KRAB to either the p13-E11 region or DUX4 exon 3 had no effect on DUX4-fl expression (FIG. 3A, lanes 3, 8). In contrast to this, targeting dCas9-KRAB to the DUX4 promoter or exon 1 reduced expression of DUX4-fl to ~45% of endogenous levels in FSHD myocytes (FIG. 3A, lanes 4, 6-7). Although dCas9 effectors often require targeting by multiple, non-overlapping sgRNAs to achieve significant transcriptional modulation, it was observed that in one case, a single sgRNA was effective in reducing DUX4-fl expression (FIG. 3A, lane 4), and the combination of all six sgRNAs targeting these regions showed no enhanced effect (FIG. 3A, lane 7).

Previous studies have demonstrated that in some contexts, dCas9 can inhibit transcription through steric hindrance of target regions. To determine whether the repressive effects observed were due to an obstruction mechanism rather than KRAB-mediated repression, the effect of a dCas9 variant lacking an effector domain (e.g. KRAB) was tested. Recruitment of dCas9 alone to any of the target regions did not reduce levels of DUX4-fl (FIG. 3A, lanes 9-13), demonstrating the importance of the KRAB domain for mediating DUX4-fl repression at the target regions.

Figure 3B:
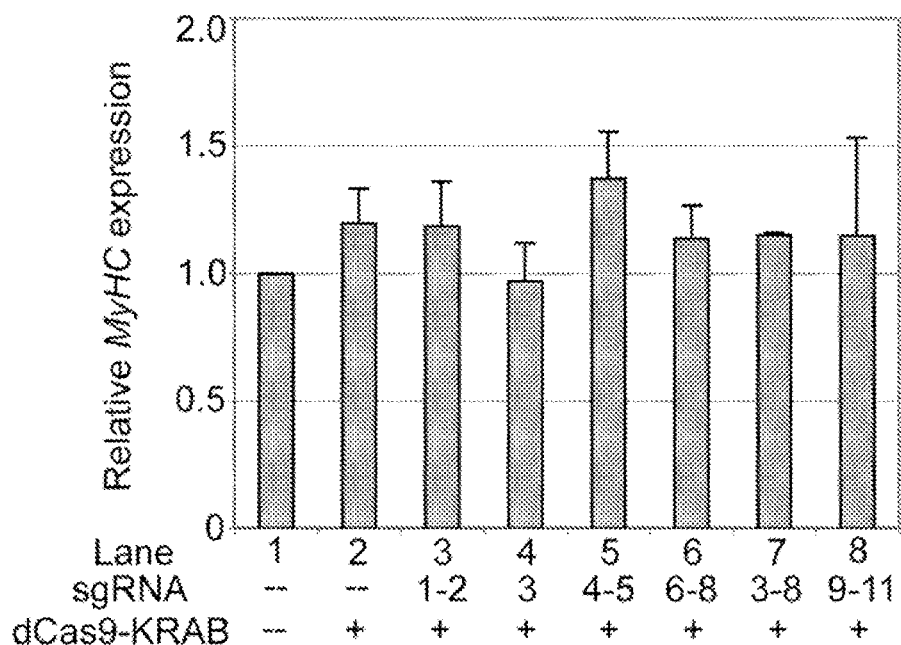
Figure 3C:
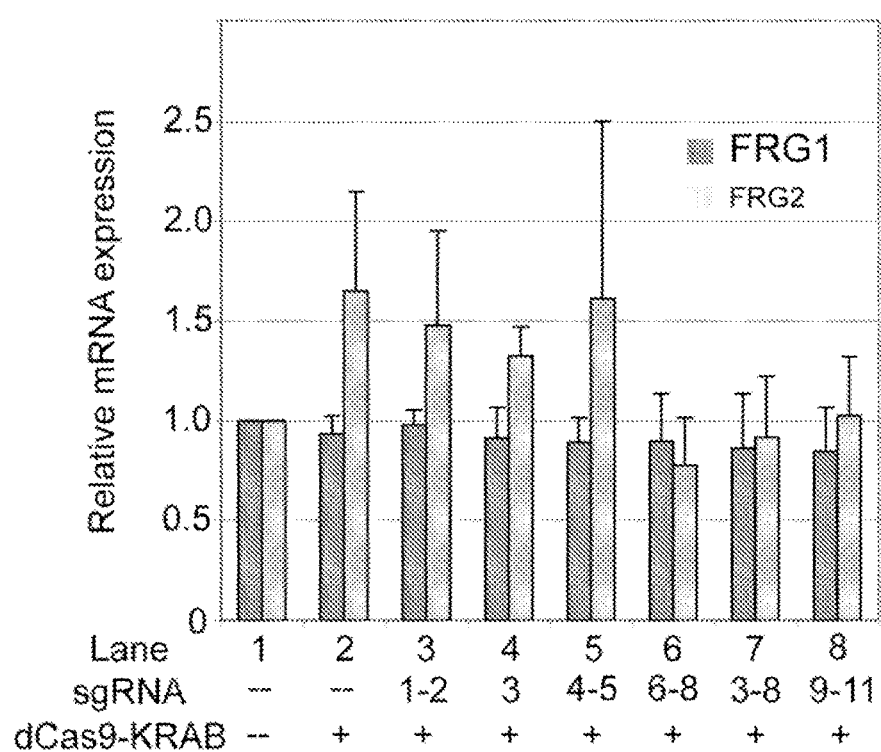

In FSHD myogenic cultures, DUX4-FL expression is restricted to terminally differentiated myocytes. To rule out a nonspecific effect of dCas9-KRAB on muscle differentiation, levels of Myosin heavy chain (MyHC), a marker of terminal muscle differentiation, were assessed by qRT-PCR. Importantly, MyHC levels were equivalent in all cultures expressing dCas9-KRAB and sgRNAs (FIG. 3B), indicating that lower levels of DUX4 fl are not due to impairment of muscle differentiation. Expression levels of FRG1 and FRG2, two other FSHD candidate genes that lie proximal to the D4Z4 repeat, were also assayed. Although levels of FRG2 were variable, recruitment of the dCas9 repressor to any of the target regions did not reduce expression of either FRG1 or FRG2 mRNA (FIG. 3C).

Figure 4:
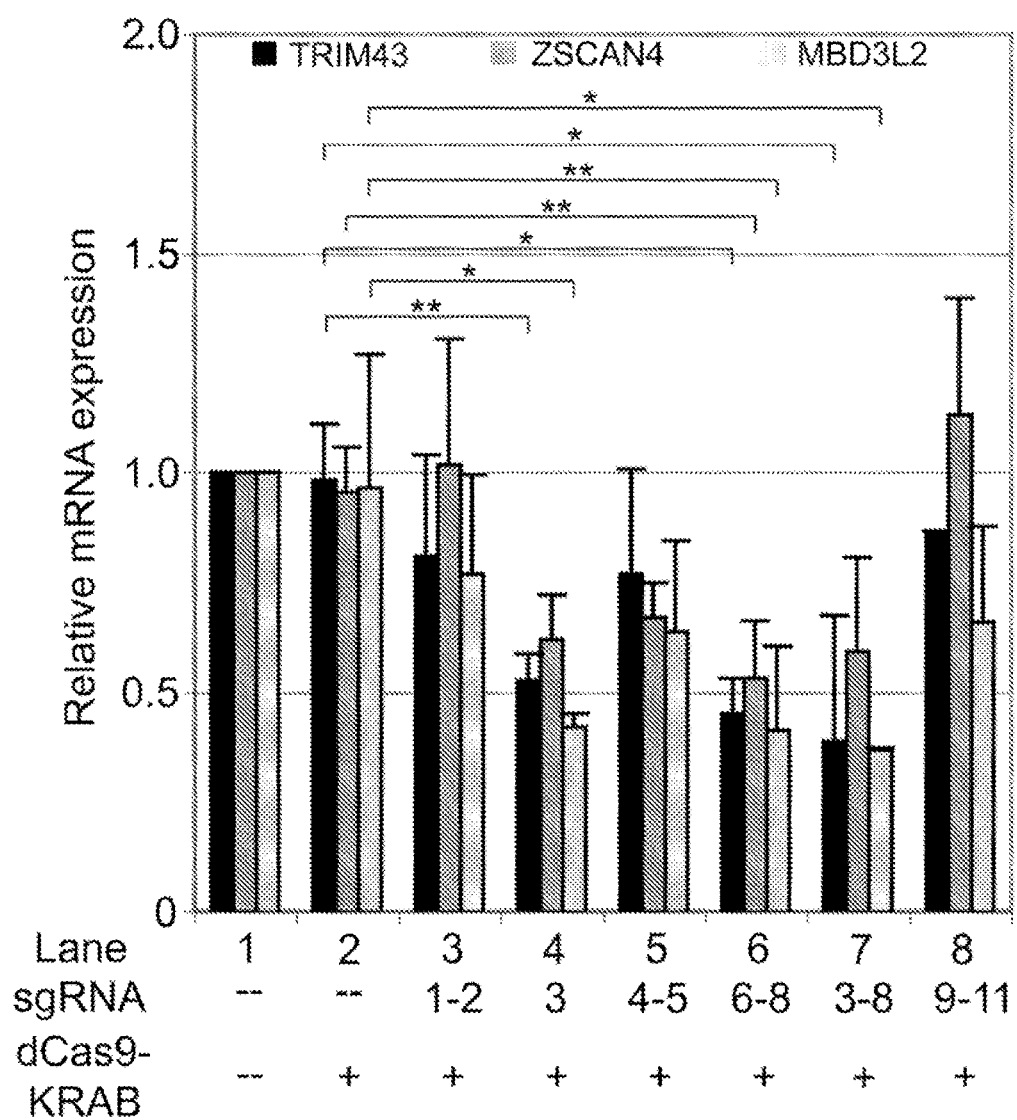
FIG. 4 shows recruitment of dCas9-KRAB to the DUX4 promoter or exon 1 represses DUX4-fl target genes in FSHD myocytes. Data relating to relative expression levels of TRIM43, ZSCAN4, and MBD3L2 are shown.

Recruitment of dCas9-KRAB to the DUX4 Promoter or exon 1 Represses DUX4-FL Targets in FSHD myocytes Expression of DUX4-FL in FSHD myocytes causes the aberrant upregulation of many downstream targets, including genes expressed in the germline and in early development. TRIM43, ZSCAN4, and MBD3L2 are downstream targets of DUX4-FL that were also found to be upregulated in the myogenic cultures used in this example. To determine whether dCas9-KRAB-mediated repression of DUX4 fl also results in repression of these DUX4-FL target genes, expression levels of TRIM43, ZSCAN4, and MBD3L2 were measured by qRT-PCR in the cells. It was observed that expression of these genes was not significantly altered by expressing the dCas9-KRAB repressor alone or by targeting the repressor to p13-E11 or to DUX4 exon 3 (FIG. 4, lanes 2,3, and 8). However, as with DUX4-fl, targeting the KRAB repressor to the DUX4 promoter or exon 1 significantly reduced expression of all three DUX4-FL targets to ~35-60% of endogenous levels (FIG. 4, lanes 4, 6-7). Thus, targeting dCas9-KRAB to the promoter or exon 1 of DUX4 results in efficient repression of both DUX4 fl and its target genes in FSHD myocytes.

Figure 5:
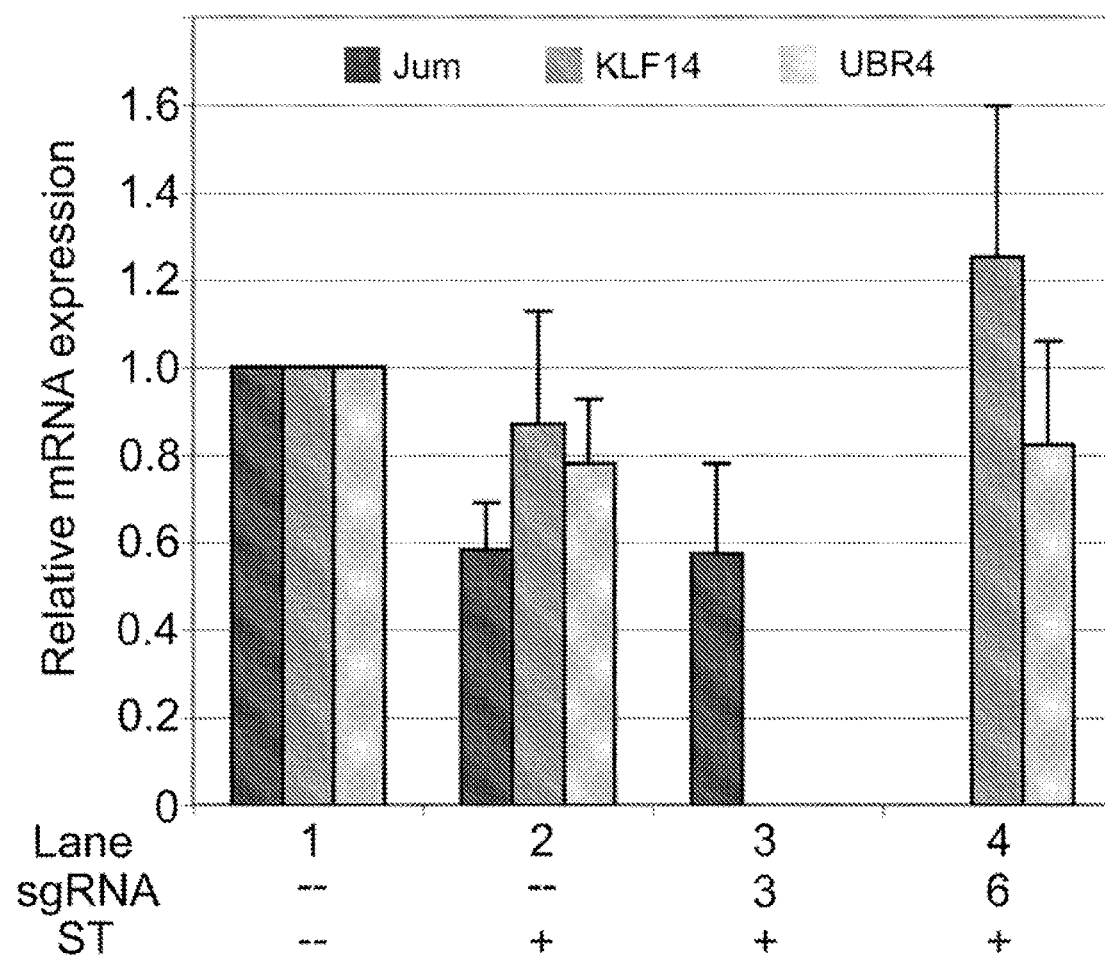
FIG. 5 shows targeting a transcriptional effector to the DUX4 promoter or exon 1 has no effect on expression of several off-target genes. Relative expression levels of Jumonji, KLF14, and UBR4 were assessed by quantitative RT-PCR after targeting of dCas9 fused to a transcriptional activator using sgRNA #3 (DUX4 promoter) or sgRNA #6 (DUX4 exon 1).

Next, the question of whether targeting a transcriptional effector to the DUX4 promoter or exon 1 has any effect on the expression of several predicted off-target genes was addressed. Of the sgRNAs used in this example to decrease expression of DUX4 fl and its downstream targets, #3 and #6 have the fewest off-target matches in the human genome (Table 1). The expression levels of several genes at a range of distances from off-target matches to sgRNAs #3 and #6 were examined in cells expressing the SunTag activator and either sgRNA. Since the binding specificity of an sgRNA is largely determined by the PAM-proximal sequence, genes in the vicinity of off-target matches to 9- or 12-bp seed sequences+NGG (PAM) were identified. For sgRNA #3, expression level of the histone demethylase Jumonji, which contains an off-target match (12-bp seed+PAM) in intron 7, was quantified. It was observed that expression of the untargeted SunTag system alone had a slight repressive effect on levels of Jumonji (FIG. 5 lane 2). However, targeting the activator with sgRNA #3 did not alter these levels (FIG. 5, lane 3). For sgRNA #6, expression levels of the transcription factor KLF14 and the E3 ubiquitin ligase UBR4, which lie 28 and 76 kb downstream of off-target matches (9 bp seed+PAM), were quantified. Neither gene showed altered expression in response to targeting the SunTag activator with this sgRNA (FIG. 5, lane 4). These results are in stark contrast to the robust targeted activation of DUX4 fl (~30-fold and ~130-fold activation using sgRNAs #3 and #6, respectively; FIG. 2B), and are consistent with the reports demonstrating limited off-target effects using dCas9 transcriptional effectors.

Figure 6A:
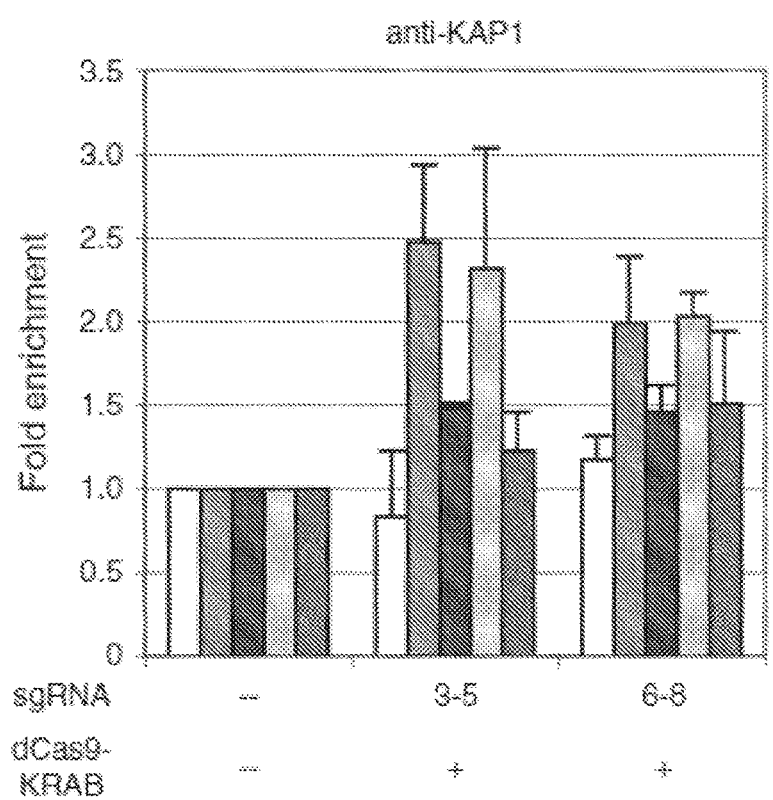
FIGS. 6A-6F show recruitment of dCas9-KRAB to the DUX4 promoter or exon 1 represses the D4Z4 locus in FSHD myocytes. Chromatin was immunoprecipitated using antibodies specific for (FIG. 6A) KAP1, (FIG. 6B) HP1α, (FIG. 6C) HP1β, (FIG. 6D) H3K27ac, or (FIG. 6E) the elongating form of RNA Pol II (Pol II-PS2), and analyzed by qPCR using primers to the (FIG. 6F) p13-E11 region of 4q35 or exon 1, intron 1, or exon 3 of DUX4 (as shown from left to right in each of FIGS. 6A-6E). Location of primers is shown in FIG. 1a. In cases where enrichment of the specific factor was observed across the DUX4 locus, an off-target region was also assessed. Data are presented as fold enrichment of the target region by each specific antibody normalized to α-histone H3, with enrichment for the mock-infected cells set to 1.
Figure 6B:
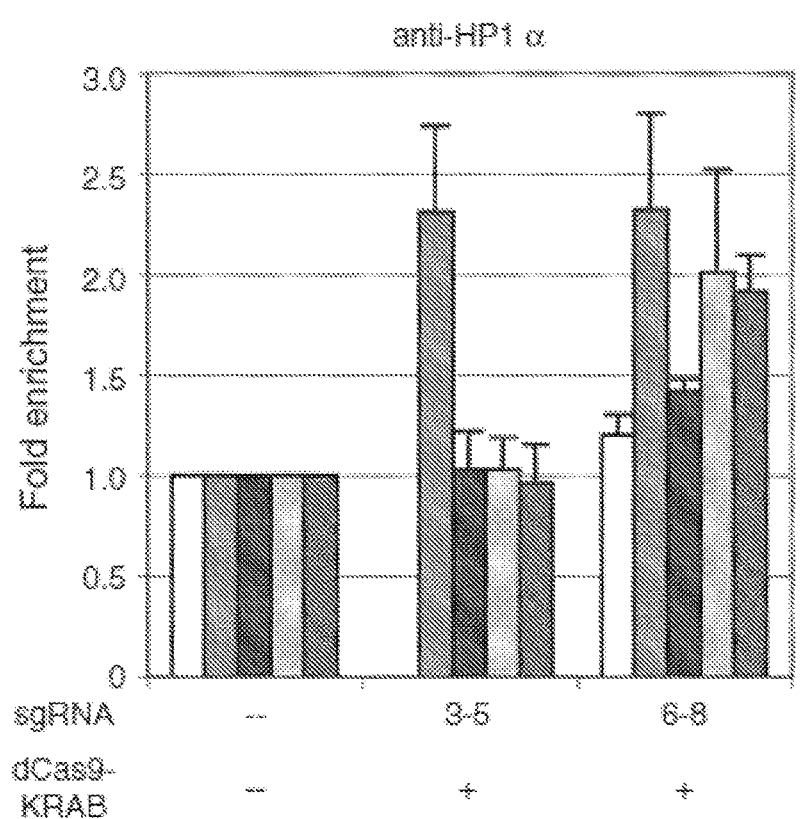
Figure 6C:
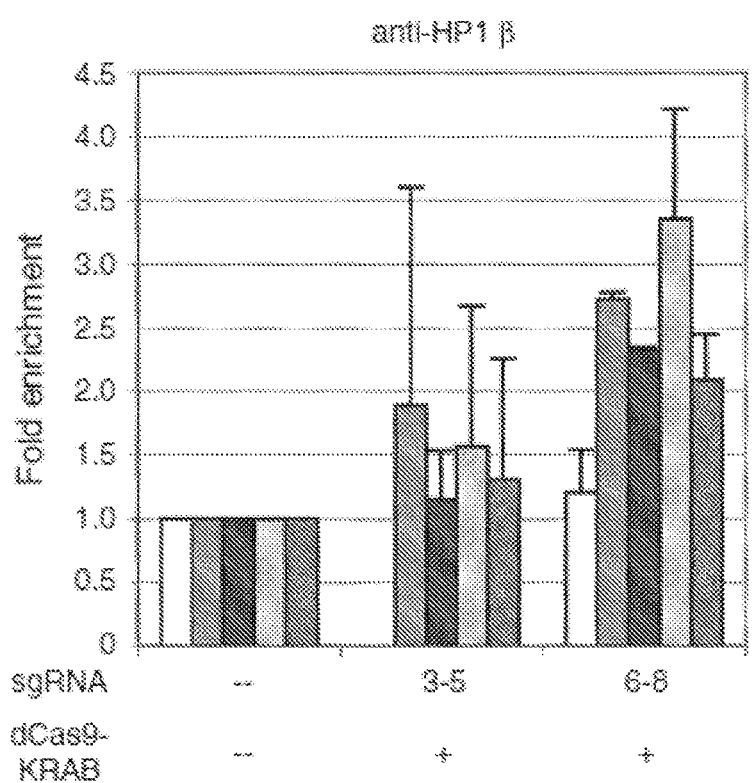
Figure 6D:
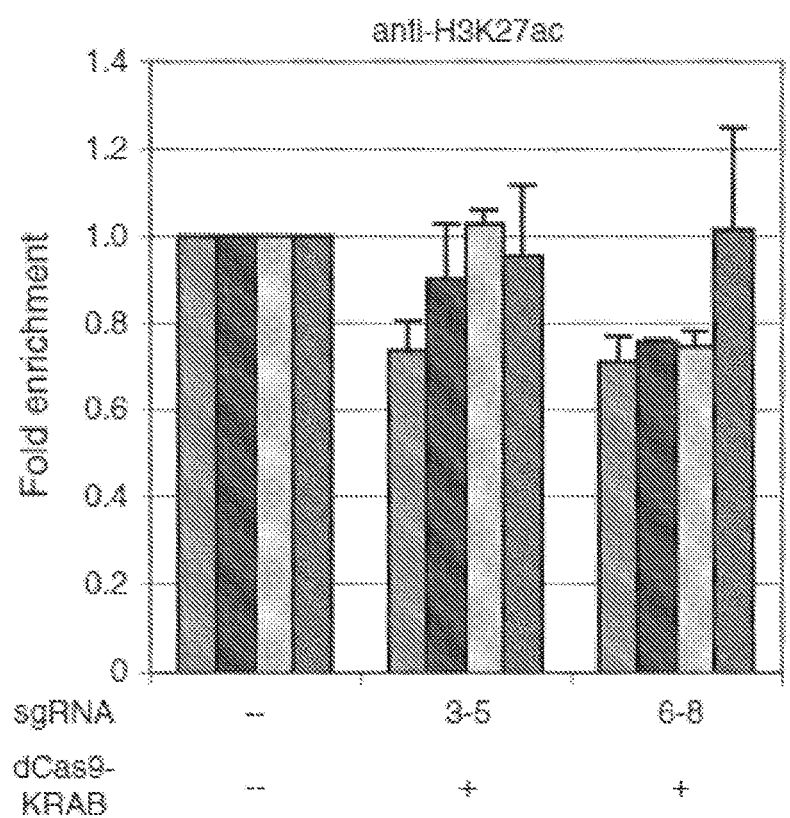

Recruitment of dCas9-KRAB to the DUX4 Promoter or exon 1 Represses the D4Z4 locus in FSHD myocytes To determine whether changes in the D4Z4 chromatin structure could be detected, FSHD myogenic cultures were infected with lentiviral supernatants expressing dCas9-KRAB and sgRNAs targeting the DUX4 promoter or exon 1, and cells were induced to differentiate, then fixed and harvested~40 hours later for analysis by ChIP. Recruitment of the dCas9 repressor to the DUX4 promoter resulted in a trend toward increased levels of the KAP1/TRIM28 corepressor, which is recruited by the KRAB domain, as well as HP1α and HP1β, which are recruited by KAP1 to heterochromatin (FIGS. 6A-6C, sgRNAs #6-8). These repressive changes were detectable across DUX4 as well as in the proximal p13-E11 region; levels of enrichment of ~2-3-fold were observed. Changes in overall levels of the repressive histone marks H3K9me3 and H3K27me3 were undetectable across the D4Z4 repeats, and targeting dCas9-KRAB to the DUX4 promoter resulted in only a slight decrease in the activating H3K27ac mark across DUX4 exon 1, intron 1, and p13-E11 (FIG. 6D, sgRNAs #6-8).

Figure 6E:
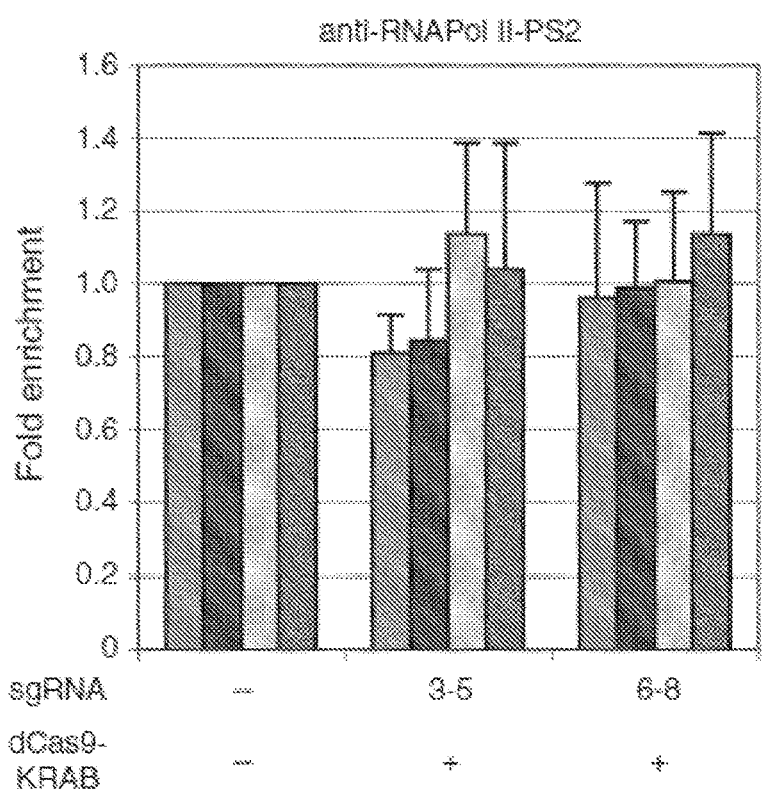
Figure 6F:
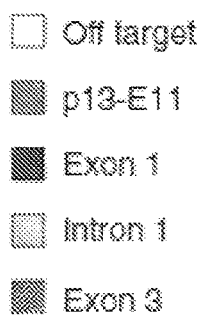

Recruitment of the dCas9 repressor to DUX4 exon 1 increased levels of KAP1 at DUX4 intron 1, but had little observable effect on levels of HP1 or H3K27 acetylation across the gene (FIGS. 6A-6D, sgRNAs #3-5). By contrast, repressive changes (enrichment of KAP1 and HP1α, and slightly reduced levels of H3K27 acetylation) were more readily detected at p13-E11, likely as a result of recruitment to the NDE (FIGS. 6A-6D, sgRNAs #3-5). There was also a trend toward slightly lower levels of elongating RNA Pol II at both exon 1 of DUX4 and p13-E11 (FIG. 6E, sgRNAs #3-5). The observed results are consistent with a model in which recruitment of dCas9-KRAB to the DUX4 promoter and exon 1 increases chromatin repression at the contracted 4q locus, resulting in decreased expression of the pathogenic DUX4 fl transcript.

In Vivo Experiments

Figure 7:
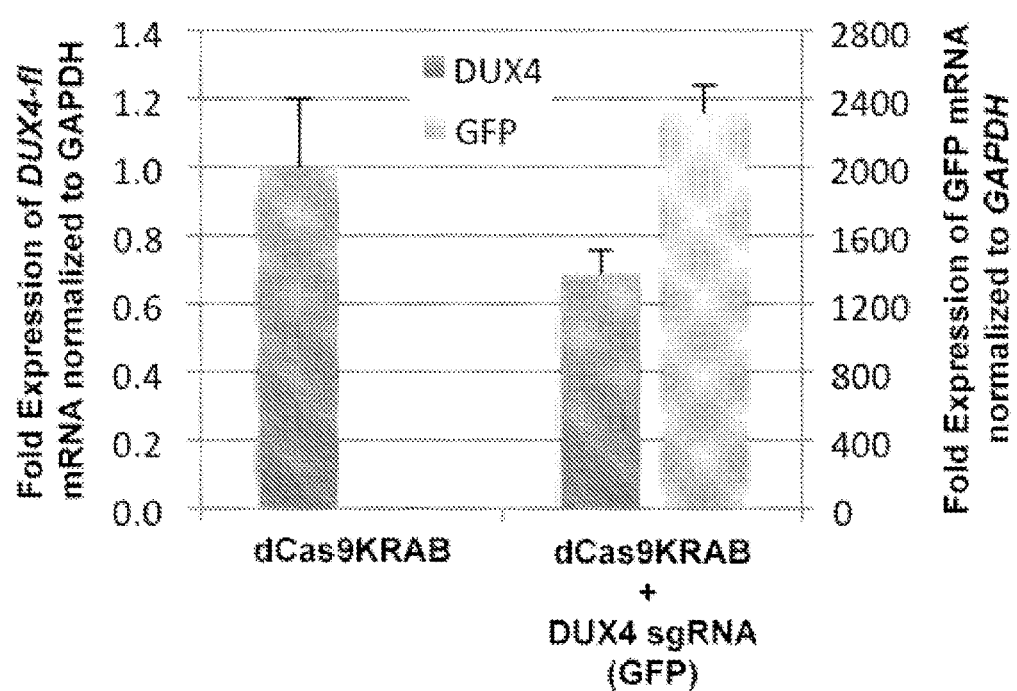
FIG. 7 shows data relating to repression of DUX4-fl expression in vivo by recruitment of dCas9-KRAB to the FSHD locus by sgRNAs in a mouse model of FSHD.

Repression of DUX4-fl in vivo was examined in a mouse model of FSHD. Mice were injected intramuscularly (IM) into Tibialis anterior (TA) muscle with AAV-dCas9KRAB and GFP-labeled DUX4 sgRNA. Relative expression level of DUX4-fl mRNA was measured and normalized to GAPDH. FIG. 7 shows data indicating that recruitment of dCas9-KRAB by DUX4 sgRNA represses DUX4-fl expression in vivo. A 30% reduction in DUX4-fl expression level was observed in mice injected with DUX4 sgRNA and dCas9KRAB compared to control mice injected with dCas9KRAB alone.

Catalytically Active Cas9 Nuclease Targeted by DUX4 sgRNA

Figure 8:
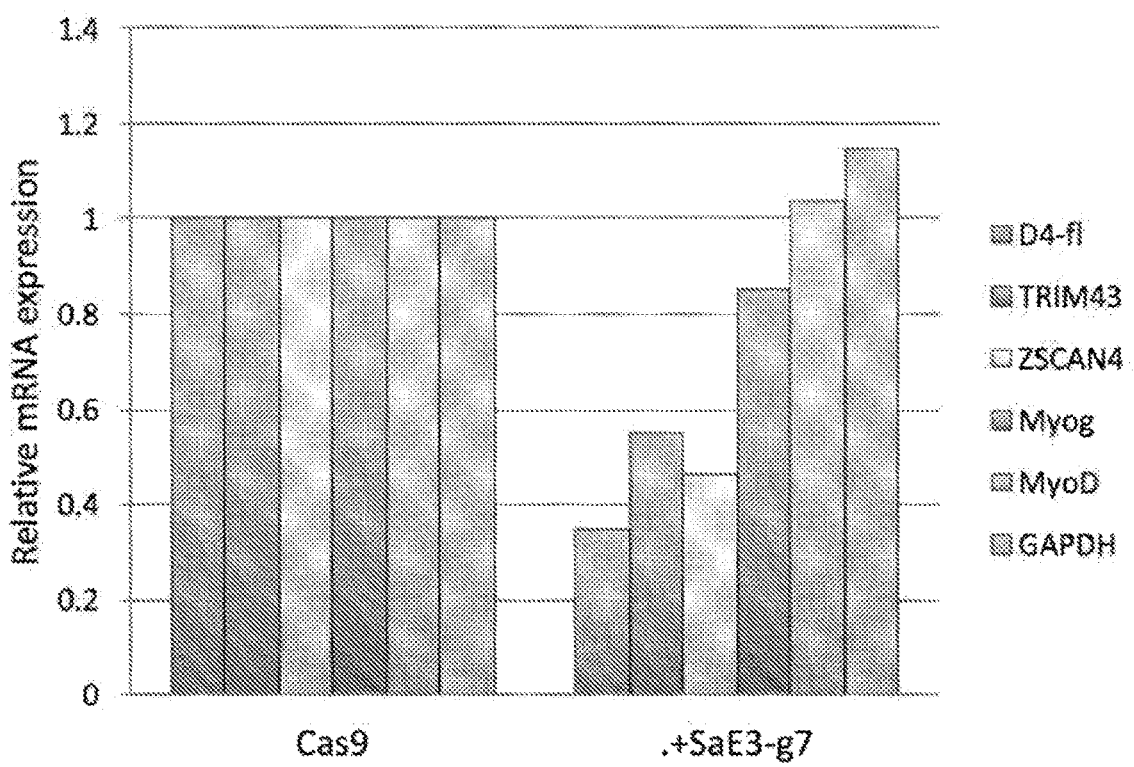
FIG. 8 shows Cas9 nuclease targeted to DUX4 exon 3 decreases expression of DUX4-fl and target genes (e.g., TRIM43, ZSCAN4) but not MyoG or MyoD. Relative expression of GAPDH is also shown as a control.

AAV-compatible, catalytically active SpCas9 was recruited to the FSHD locus in primary human myogenic cells by using sgRNA targeting exon 3 of the DUX4 gene. Targeting of the Cas9 nuclease to exon 3 of DUX4 resulted in reduction of DUX4 expression as quantified by relative mRNA expression (FIG. 8). Decreased expression of DUX4 also resulted in reduced relative expression of DUX4 target genes, such as TRIM43 and ZSCAN4, but not the muscle-specific genes MyoG or MyoD (FIG. 8).

TABLE 1 sgRNA sequences targeting the D4Z4/DUX4 region

| sgRNA (SEQ ID NO:) | Target | *19-nt sequence + PAM (NGG) | Score** | Enrich^ | OT(12)# | OT(19)## |
|---|---|---|---|---|---|---|
| 1 | p13-E11 | TACCACAGACAGCCAACTGGGG | 0.61 | 6.9 | 18 | 0 |
| 2 | p13-E11 | TTCACCCAGAACAGTAACTGGG | 0.60 | 1.6 | 27 | 0 |
| 3 | DUX4 E1 | CACCCGGGCAAAAGCCGGGAGG | 0.61 | 2.5 | 8 | 1 (Y) |
| 4 | DUX4 E1 | CTGGAAGCACCCCTCAGCGAGG | 0.85 | 2.4 | 9 | 3 (14/18/Y) |
| 5 | DUX4 E1 | CTGGAGGAGCTTTAGGACGCGG | 0.65 | 2.2 | 14 | 6 (14/18/20/22/Y) |
| 6 | DUX4 prom | CTCGCTCTGGTCTTCTACGTGG | 0.72 | 2.0 | 4 | 0 |
| 7 | DUX4 prom | CCGTCCGTGAAATTCCGGCCGG | 0.76 | 1.7 | 10 | 1 (20) |
| 8 | DUX4 prom | TCGGACAGCACCCTCCCCGCGG | 0.79 | 2.6 | 19 | 3 (3/14/Y) |
| 9 | DUX4 E3 | CTCCCTTGCACGTCAGCCGGGG | 0.84 | 3.4 | 7 | 2 (14/18) |
| 10 | DUX4 E3 | GAATTTCACGGAAGAACAAGGG | 0.76 | 1.8 | 5 | 0 |
| 11 | DUX4 E3 | ATCTTCTATAGGATCCACAGGG | 0.88 | 2.0 | 9 | 0 |

CpGs are underlined
**sgRNA Designer score.
^Relative enrichment of dCas9-VP64-HA (Addgene plasmid #50918) at each target region measured by chromatin immunoprecipitation (ChIP) using HA antibodies normalized to mouse IgG.
Number of off-target (non-Ch 4/10) matches to 12-nt seed sequence + NGG in human genomic database.
Number of off-target (non-Ch 4/10) matches to 19-nt sequence + NGG in human genomic database (chromosomes in parentheses).

All off-target matches except those underlined are in D4Z4 homologous repeat sequences.

TABLE 2

Primer sequences

| Primer Name | Sequence (5'-3') | SEQ ID NO: |
|---|---|---|
| DUX4-f1-F | GCTCTGCTGGAGGAGCTTTAGGA | 12 |
| DUX4-f1-R | GCAGGTCTGCWGGTACCTGG | 13 |
| MyHC1-F | TGGAGGCCAGGGTTCGTGAA | 14 |
| MyHC1-R | ATTGTTCCTCCGCTTCTTCAGC | 15 |
| FRG1-F | TCTACAGAGACGTAGGCTGTCA | 16 |
| FRG1-R | CTTGAGCACGAGCTTGGTAG | 17 |
| FRG2-F | GGGAAAACTGCAGGAAAA | 18 |
| FRG2-R | CTGGACAGTTCCCTGCTGTGT | 19 |
| TRIM43-F | ACCCATCACTGGACTGGTGT | 20 |
| TRIM43-R | CACATCCTCAAAGAGCCTGA | 21 |

TABLE 2-continued

Primer sequences

| Primer Name | Sequence (5'-3') | SEQ ID NO: |
|---|---|---|
| ZSCAN4-F | TGGAAATCAAGTGGCAAAAA | 22 |
| ZSCAN4-R | CTGCATGTGGACGTGGAC | 23 |
| MBD3L2-F | GCGTTCACCTCTTTTCCAAG | 24 |
| MBD3L2-R | GCCATGTGGATTTCTCGTTT | 25 |
| Jumonji-F | AAGAAAAAGCCTCGAAAGTG | 26 |
| Jumonji-R | AGAGCACACTCCAGACAGAA | 27 |
| KLF14-F | TGCAACGTGTATATCATCCT | 28 |
| KLF14-R | ACACCAGAGTCCTTTGAGAC | 29 |
| UBR4-F | GGAGTCTGTGGCAACTGTGGAGAGAATG | 30 |
| UBR4-R | CCGGTCTTCTTCATTCTCAATGGGATCCACT | 31 |
| OT-F* | GAATGTGGACACGGTAAAGA | 32 |
| OT-R** | TAGGTTTGACTGCCAATGAC | 33 |
| p13-E11-F | TGGGCATTTTCTCATTAGCC | 34 |
| p13-E11-R | CTGGAGCAGAGATGACCACA | 35 |
| DUX4-exon1-F | GACACCCTCGGACAGCAC | 36 |
| DUX4-exon1-R | GTACGGGTTCCGCTCAAAG | 37 |
| DUX4-intron1-F | CTCAGCGAGGAAGAATACCG | 38 |
| DUX4-intron1-R | AGTCTCTCACCGGGCCTAGA | 39 |
| DUX4-exon3-F | CTGACGTGCAAGGGAGCT | 40 |
| DUX4-exon3-R | CAGGTTTGCCTAGACAGCG | 41 |

*OT-F: (intergenic region on Ch. 8, ref NC_018919.2)
**OT-R: (intergenic region on Ch. 8, ref NC_018919.2)

SaCas9 Protein (SEQ ID NO: 42)
MAPKKKRKVGIHGVPAAKRNYILGLAIGITSVGYGIIDYETRDVIDAGVRL
FKEANVENNEGRRSKRGARRLKRRRRHRIQRVKKLLFDYNLLTDHSELSGI
NPYEARVKGLSQKLSEEEFSAALLHLAKRRGVHNVNEVEEDTGNELSTKEQ
ISRNSKALEEKYVAELQLERLKKDGEVRGSINRFKTSDYVKEAKQLLKVQK
AYHQLDQSFIDTYIDLLETRRTYYEGPGEGSPFGWKDIKEWYEMLMGHCTY
FPEELRSVKYAYNADLYNALNDLNNLVITRDENEKLEYYEKFQIIENVFKQ
KKKPTLKQIAKEILVNEEDIKGYRVTSTGKPEFTNLKVYHDIKDITARKEI
IENAELLDQIAKILTIYQSSEDIQEELTNLSELTQEEIEQISNLKGYTGT
HNLSLKAINLILDELWHTNDNQIAIFNRLKLVPKKVDLSQQKEIPTTLVDD
FILSPVVKRSFIQSIKVINAIIKKYGLPNDIIIELAREKNSDAQKMINEM
QKRNRQTNERIEEIIRTTGKENAKYLIEKIKLHDMQEGKCLYSLEAIPLED
LLNNPFNYEVDHIIPRSVSFDNSFNNKVLVKQEENSKKGNRTPFQYLSSSD
SKISYETFKKHILNLAKGKGRISKTKKEYLLEERDINRFSVQKDFINRNLV
DTRYATRGLMNLLRSYFRVNNLDVKVKSINGGFTSFLRRKWKFKKERNKGY
KHHAEDALIIANADFIFKEWKKLDKAKKVMENQMFEEKQAESMPEIETEQE
YKEIFITPHQIKHIKDFKDYKYSHRVDKKPNRELINDTLYSTRKDDKGNTL
IVNNLNGLYDKDNDKLKKLINKSPEKLLMYHHDPQTYQKLKLIMEQYGDEK
NPLYKYYEETGNYLTKYSKKDNGPVIKKIKYYGNKLNAHLDITDDYPNSRN
KVVKLSLKPYRFDVYLDNGVYKFVTVKNLDVIKKENYYEVNSKCYEEAKKL
KKISNQAEFIASFYNNDLIKINGELYRVIGVNNDLLNRIEVNMIDITYREY
LENMNDKRPPIIKTIASKTQSIKKYSTDILGNLYEVKSKKHPQIIKKGKR
PAATKKAGQAK Sa-dCas9-KRAB (SEQ ID NO: 43)
MAPKKKRKVGIHGVPAAKRNYILGLAIGITSVGYGIIDYETRDVIDAGVRL
FKEANVENNEGRRSKRGARRLKRRRRHRIQRVKKLLFDYNLLTDHSELSGI
NPYEARVKGLSQKLSEEEFSAALLHLAKRRGVHNVNEVEEDTGNELSTKEQ
ISRNSKALEEKYVAELQLERLKKDGEVRGSINRFKTSDYVKEAKQLLKVQK
AYHQLDQSFIDTYIDLLETRRTYYEGPGEGSPFGWKDIKEWYEMLMGHCTY
FPEELRSVKYAYNADLYNALNDLNNLVITRDENEKLEYYEKFQIIENVFKQ
KKKPTLKQIAKEILVNEEDIKGYRVTSTGKPEFTNLKVYHDIKDITARKEI
IENAELLDQIAKILTIYQSSEDIQEELTNLSELTQEEIEQISNLKGYTGT
HNLSLKAINLILDELWHTNDNQIAIFNRLKLVPKKVDLSQQKEIPTTLVDD
FILSPVVKRSFIQSIKVINAIIKKYGLPNDIIIELAREKNSDAQKMINEM
QKRNRQTNERIEEIIRTTGKENAKYLIEKIKLHDMQEGKCLYSLEAIPLED
LLNNPFNYEVDHIIPRSVSFDNSFNNKVLVKQEEASKKGNRTPFQYLSSSD
SKISYETFKKHILNLAKGKGRISKTKKEYLLEERDINRFSVQKDFINRNLV
DTRYATRGLMNLLRSYFRVNNLDVKVKSINGGFTSFLRRKWKFKKERNKGY
KHHAEDALIIANADFIFKEWKKLDKAKKVMENQMFEEKQAESMPEIETEQE
YKEIFITPHQIKHIKDFKDYKYSHRVDKKPNRELINDTLYSTRKDDKGNTL
IVNNLNGLYDKDNDKLKKLINKSPEKLLMYHHDPQTYQKLKLIMEQYGDEK
NPLYKYYEETGNYLTKYSKKDNGPVIKKIKYYGNKLNAHLDITDDYPNSRN
KVVKLSLKPYRFDVYLDNGVYKFVTVKNLDVIKKENYYEVNSKCYEEAKKL
KKISNQAEFIASFYNNDLIKINGELYRVIGVNNDLLNRIEVNMIDITYREY
LENMNDKRPPIIKTIASKTQSIKKYSTDILGNLYEVKSKKHPQIIKKGKR
PAATKKAGQAKKKGSDAKSLTAWSRTLVTFKDVFVDFTREEWKLLDTAQQ
IVYRNVMLENYKNLVSLGYQLTKPDVILRLEKGEEP Sp-dCas9-KRAB (SEQ ID NO: 44)
MDKKYSIGLAIGTNSVGWAVITDEYKVPSKKFKVLGNTDRHSIKKNLIGAL
LFDSGETAEATRLKRTARRRYTRRKNRICYLQEIFSNEMAKVDDSFFHRLE
ESFLVEEDKKHERHPIFGNIVDEVAYHEKYPTIYHLRKKLVDSTDKADLRL
IYLALAHMIKFRGHFLIEGDLNPDNSDVDKLFIQLVQTYNQLFEENPINAS
GVDAKAILSARLSKSRRLENLIAQLPGEKKNGLFGNLIALSLGLTPNFKSN
FDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGN
SRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTV
KQLKEDYFKKIECFDSVETSGVEDRFNASLGTYHDLLKIIKDKDFLDNEEN
EDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVS
GQGDSLHEHIANLAGSPAIKKGILQTVKVVDELVKVMGRHKPENIVIEMAR
ENQTTQKGQKNSRERMKRIEEGIKELGSQILKEHPVENTQLQNEKLYLYYL
QNGRDMYVDQELDINRLSDYDVDAIVPQSFLKDDSIDNKVLTRSDKNRGKS
DNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKD
FQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGE
IVWDKGRDFATVRKVLSMPQVNIVKKTEVQTGGFSKESILPKRNSDKLIAR
KKDWDPKKYGGFDSPTVAYSVLVVAKVEKGKSKKLKSVKELLGITIMERSS
FEKNPIDFLEAKGYKEVKKDLIIKLPKYSLFELENGRKRMLASAGELQKGN
ELALPSKYVNFLYLASHYEKLKGSPEDNEQKQLFVEQHKHYLDEIIEQISE
FSKRVILADANLDKVLSAYNKHRDKPIREQAENIIHLFTLTNLGAPAAFKY
FDTTIDRKRYTSTKEVLDATLIHQSITGLYETRIDLSQLGGDGTGGPKKKR
KVYPYDVPDYAGYPYDVPDYAGSYPYDVPDYAGSMDAKSLTAWSRTLVTFK
DVFVDFTREEWKLLDTAQQIVYRNVMLENYKNLVSLGYQLTKPDVILRLEK
GEEP Sa-dCas9 (SEQ ID NO: 45)
MAPKKKRKVGIHGVPAAKRNYILGLAIGITSVGYGIIDYETRDVIDAGVRL
FKEANVENNEGRRSKRGARRLKRRRRHRIQRVKKLLFDYNLLTDHSELSGI
NPYEARVKGLSQKLSEEEFSAALLHLAKRRGVHNVNEVEEDTGNELSTKEQ
ISRNSKALEEKYVAELQLERLKKDGEVRGSINRFKTSDYVKEAKQLLKVQK
AYHQLDQSFIDTYIDLLETRRTYYEGPGEGSPFGWKDIKEWYEMLMGHCTY
FPEELRSVKYAYNADLYNALNDLNNLVITRDENEKLEYYEKFQIIENVFKQ
KKKPTLKQIAKEILVNEEDIKGYRVTSTGKPEFTNLKVYHDIKDITARKEI
IENAELLDQIAKILTIYQSSEDIQEELTNLSELTQEEIEQISNLKGYTGT
HNLSLKAINLILDELWHTNDNQIAIFNRLKLVPKKVDLSQQKEIPTTLVDD
FILSPVVKRSFIQSIKVINAIIKKYGLPNDIIIELAREKNSDAQKMINEM
QKRNRQTNERIEEIIRTTGKENAKYLIEKIKLHDMQEGKCLYSLEAIPLED
LLNNPFNYEVDHIIPRSVSFDNSFNNKVLVKQEEASKKGNRTPFQYLSSSD
SKISYETFKKHILNLAKGKGRISKTKKEYLLEERDINRFSVQKDFINRNLV
DTRYATRGLMNLLRSYFRVNNLDVKVKSINGGFTSFLRRKWKFKKERNKGY
KHHAEDALIIANADFIFKEWKKLDKAKKVMENQMFEEKQAESMPEIETEQE
YKEIFITPHQIKHIKDFKDYKYSHRVDKKPNRELINDTLYSTRKDDKGNTL
IVNNLNGLYDKDNDKLKKLINKSPEKLLMYHHDPQTYQKLKLIMEQYGDEK
NPLYKYYEETGNYLTKYSKKDNGPVIKKIKYYGNKLNAHLDITDDYPNSRN
KVVKLSLKPYRFDVYLDNGVYKFVTVKNLDVIKKENYYEVNSKCYEEAKKL
KKISNQAEFIASFYNNDLIKINGELYRVIGVNNDLLNRIEVNMIDITYREY
LENMNDKRPPIIKTIASKTQSIKKYSTDILGNLYEVKSKKHPQIIKKG

What is claimed is:

1. A recombinant gene editing complex comprising:
   (i) a recombinant gene editing protein; and,
   (ii) a nucleic acid encoding a guide RNA (gRNA) that specifically hybridizes to a target nucleic acid sequence encoding a D4Z4 macrosatellite repeat region, wherein the gRNA comprises a sequence encoded by the sequence set forth in any one of SEQ ID NOs: 1-11, wherein binding of the complex to the target nucleic acid sequence results in inhibition of DUX4 gene expression.

2. The recombinant gene editing complex of claim 1, wherein the target nucleic acid sequence is located on chromosome 4 at position 4q35.

3. The recombinant gene editing complex of claim 1, wherein the gRNA specifically hybridizes to a nucleic acid sequence encoding a DUX4 promoter or exon 1 of DUX4.

4. The recombinant gene editing complex of claim 1, wherein the gRNA comprises a sequence encoded by the sequence set forth in any one of SEQ ID NOs: 3-8.

5. The recombinant gene editing complex of claim 1, wherein the recombinant gene editing protein comprises a Cas protein, a Cfp1 protein, or a variant thereof.

6. The recombinant gene editing complex of claim 5, wherein the Cas protein is
   (i) a *Streptococcus pyogenes* Cas protein or a *Staphylococcus aureus* Cas protein; or
   (ii) a Cas9 protein or a dead Cas9 (dCas9) protein.

7. The recombinant gene editing complex of claim 5, wherein the recombinant gene editing protein comprises the sequence set forth in SEQ ID NO: 45.

8. The recombinant gene editing complex of claim 1, wherein the recombinant gene editing protein further comprises a transcriptional repressor domain.

9. The recombinant gene editing complex of claim 8, wherein the transcriptional repressor domain is a KRAB domain.

10. The recombinant gene editing complex of claim 9, wherein the gene editing protein comprises the sequence set forth in SEQ ID NO: 43 or 44.

11. A vector comprising a nucleic acid encoding the recombinant gene editing complex of claim 1.

12. The vector of claim 11, wherein the nucleic acid is engineered to express the recombinant gene editing complex in a cell.

13. The vector of claim 11, wherein the vector is a lentiviral vector or a recombinant adeno-associated virus vector (rAAV vector).

* * * * *

SEQUENCE LISTING

<160> NUMBER OF SEQ ID NOS: 45

<210> SEQ ID NO 1
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 1
taccacagac agccaactgg gg                                                  22

<210> SEQ ID NO 2
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 2
ttcacccaga acagtaactg gg                                                  22

<210> SEQ ID NO 3
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 3
cacccgggca aaagccggga gg                                                  22

<210> SEQ ID NO 4
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 4
ctggaagcac ccctcagcga gg                                                  22

<210> SEQ ID NO 5
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 5
ctggaggagc tttaggacgc gg                                                  22

<210> SEQ ID NO 6
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 6
ctcgctctgg tcttctacgt gg                                                  22

<210> SEQ ID NO 7
<211> LENGTH: 22
<212> TYPE: DNA
<213> ORGANISM: Artificial Sequence

```
<220> FEATURE:
<223> OTHER INFORMATION: Synthetic polynucleotide

<400> SEQUENCE: 7
ccgtccgtga aattccggcc gg                                            22

<210> SEQ ID NO 8
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 8
tcggacagca ccctccccgc gg                                            22

<210> SEQ ID NO 9
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 9
ctcccttgca cgtcagccgg gg                                            22

<210> SEQ ID NO 10
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 10
gaatttcacg gaagaacaag gg                                            22

<210> SEQ ID NO 11
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 11
atcttctata ggatccacag gg                                            22

<210> SEQ ID NO 12
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 12
gctctgctgg aggagcttta gga                                           23

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
gcaggtctgc wggtacctgg                                               20
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
tggaggccag ggttcgtgaa                                              20

<210> SEQ ID NO 15
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 15
attgttcctc cgcttcttca gc                                           22

<210> SEQ ID NO 16
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 16
tctacagaga cgtaggctgt ca                                           22

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
cttgagcacg agcttggtag                                              20

<210> SEQ ID NO 18
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 18
gggaaaactg caggaaaa                                                18

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 19
ctggacagtt ccctgctgtg t                                            21

<210> SEQ ID NO 20
<211> LENGTH: 20
<212> TYPE: DNA
<213> ORGANISM: Artificial Sequence
<220> FEATURE:
<223> OTHER INFORMATION: Synthetic polynucleotide
```

```
<400> SEQUENCE: 20
acccatcact ggactggtgt                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
cacatcctca aagagcctga                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
tggaaatcaa gtggcaaaaa                                              20

<210> SEQ ID NO 23
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 23
ctgcatgtgg acgtggac                                                18

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24
gcgttcacct cttttccaag                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
gccatgtgga tttctcgttt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
aagaaaaagc ctcgaaagtg                                              20

<210> SEQ ID NO 27
```

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
agagcacact ccagacagaa                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
tgcaacgtgt atatcatcct                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
acaccagagt cctttgagac                                               20

<210> SEQ ID NO 30
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 30
ggagtctgtg gcaactgtgg agagaatg                                      28

<210> SEQ ID NO 31
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 31
ccggtcttct tcattctcaa tgggatccac t                                  31

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
gaatgtggac acggtaaaga                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 33
```

```
taggtttgac tgccaatgac                                            20

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
tgggcatttt ctcattagcc                                            20

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
ctggagcaga gatgaccaca                                            20

<210> SEQ ID NO 36
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 36
gacaccctcg gacagcac                                              18

<210> SEQ ID NO 37
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 37
gtacgggttc cgctcaaag                                             19

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
ctcagcgagg aagaataccg                                            20

<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 39
agtctctcac cgggcctaga                                            20

<210> SEQ ID NO 40
<211> LENGTH: 18
<212> TYPE: DNA
```

<213> ORGANISM: Artificial Sequence
<220> FEATURE:
<223> OTHER INFORMATION: Synthetic polynucleotide

<400> SEQUENCE: 40
ctgacgtgca agggagct					18

<210> SEQ ID NO 41
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 41
caggtttgcc tagacagcg					19

<210> SEQ ID NO 42
<211> LENGTH: 1082
<212> TYPE: PRT
<213> ORGANISM: Artificial Sequence
<220> FEATURE:
<223> OTHER INFORMATION: Synthetic polypeptide

<400> SEQUENCE: 42

```
Met Ala Pro Lys Lys Arg Lys Val Gly Ile His Gly Val Pro Ala
1               5                   10                  15

Ala Lys Arg Asn Tyr Ile Leu Gly Leu Asp Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Phe Ser Ala Ala Leu Leu His Leu
        115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
    210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
```

```
            260                 265                 270
Asn Ala Leu Asn Asp Leu Asn Asn Leu Val Ile Thr Arg Asp Glu Asn
            275                 280                 285
Glu Lys Leu Glu Tyr Tyr Glu Lys Phe Gln Ile Ile Glu Asn Val Phe
            290                 295                 300
Lys Gln Lys Lys Lys Pro Thr Leu Lys Gln Ile Ala Lys Glu Ile Leu
305                 310                 315                 320
Val Asn Glu Glu Asp Ile Lys Gly Tyr Arg Val Thr Ser Thr Gly Lys
                325                 330                 335
Pro Glu Phe Thr Asn Leu Lys Val Tyr His Asp Ile Lys Asp Ile Thr
                340                 345                 350
Ala Arg Lys Glu Ile Ile Glu Asn Ala Glu Leu Leu Asp Gln Ile Ala
            355                 360                 365
Lys Ile Leu Thr Ile Tyr Gln Ser Ser Glu Asp Ile Gln Glu Glu Leu
            370                 375                 380
Thr Asn Leu Asn Ser Glu Leu Thr Gln Glu Glu Ile Glu Gln Ile Ser
385                 390                 395                 400
Asn Leu Lys Gly Tyr Thr Gly Thr His Asn Leu Ser Leu Lys Ala Ile
                405                 410                 415
Asn Leu Ile Leu Asp Glu Leu Trp His Thr Asn Asp Asn Gln Ile Ala
                420                 425                 430
Ile Phe Asn Arg Leu Lys Leu Val Pro Lys Lys Val Asp Leu Ser Gln
            435                 440                 445
Gln Lys Glu Ile Pro Thr Thr Leu Val Asp Asp Phe Ile Leu Ser Pro
            450                 455                 460
Val Val Lys Arg Ser Phe Ile Gln Ser Ile Lys Val Ile Asn Ala Ile
465                 470                 475                 480
Ile Lys Lys Tyr Gly Leu Pro Asn Asp Ile Ile Glu Leu Ala Arg
                485                 490                 495
Glu Lys Asn Ser Lys Asp Ala Gln Lys Met Ile Asn Glu Met Gln Lys
                500                 505                 510
Arg Asn Arg Gln Thr Asn Glu Arg Ile Glu Glu Ile Ile Arg Thr Thr
            515                 520                 525
Gly Lys Glu Asn Ala Lys Tyr Leu Ile Glu Lys Ile Lys Leu His Asp
            530                 535                 540
Met Gln Glu Gly Lys Cys Leu Tyr Ser Leu Glu Ala Ile Pro Leu Glu
545                 550                 555                 560
Asp Leu Leu Asn Asn Pro Phe Asn Tyr Glu Val Asp His Ile Ile Pro
                565                 570                 575
Arg Ser Val Ser Phe Asp Asn Ser Phe Asn Asn Lys Val Leu Val Lys
                580                 585                 590
Gln Glu Glu Asn Ser Lys Lys Gly Asn Arg Thr Pro Phe Gln Tyr Leu
            595                 600                 605
Ser Ser Ser Asp Ser Lys Ile Ser Tyr Glu Thr Phe Lys Lys His Ile
            610                 615                 620
Leu Asn Leu Ala Lys Gly Lys Gly Arg Ile Ser Lys Thr Lys Lys Glu
625                 630                 635                 640
Tyr Leu Leu Glu Glu Arg Asp Ile Asn Arg Phe Ser Val Gln Lys Asp
                645                 650                 655
Phe Ile Asn Arg Asn Leu Val Asp Thr Arg Tyr Ala Thr Arg Gly Leu
                660                 665                 670
Met Asn Leu Leu Arg Ser Tyr Phe Arg Val Asn Asn Leu Asp Val Lys
            675                 680                 685
```

-continued

```
Val Lys Ser Ile Asn Gly Gly Phe Thr Ser Phe Leu Arg Arg Lys Trp
690                 695                 700
Lys Phe Lys Lys Glu Arg Asn Lys Gly Tyr Lys His His Ala Glu Asp
705                 710                 715                 720
Ala Leu Ile Ile Ala Asn Ala Asp Phe Ile Phe Lys Glu Trp Lys Lys
                725                 730                 735
Leu Asp Lys Ala Lys Lys Val Met Glu Asn Gln Met Phe Glu Glu Lys
            740                 745                 750
Gln Ala Glu Ser Met Pro Glu Ile Glu Thr Glu Gln Glu Tyr Lys Glu
        755                 760                 765
Ile Phe Ile Thr Pro His Gln Ile Lys His Ile Lys Asp Phe Lys Asp
770                 775                 780
Tyr Lys Tyr Ser His Arg Val Asp Lys Lys Pro Asn Arg Glu Leu Ile
785                 790                 795                 800
Asn Asp Thr Leu Tyr Ser Thr Arg Lys Asp Asp Lys Gly Asn Thr Leu
                805                 810                 815
Ile Val Asn Asn Leu Asn Gly Leu Tyr Asp Lys Asp Asn Asp Lys Leu
            820                 825                 830
Lys Lys Leu Ile Asn Lys Ser Pro Glu Lys Leu Leu Met Tyr His His
        835                 840                 845
Asp Pro Gln Thr Tyr Gln Lys Leu Lys Leu Ile Met Glu Gln Tyr Gly
850                 855                 860
Asp Glu Lys Asn Pro Leu Tyr Lys Tyr Tyr Glu Glu Thr Gly Asn Tyr
865                 870                 875                 880
Leu Thr Lys Tyr Ser Lys Lys Asp Asn Gly Pro Val Ile Lys Lys Ile
                885                 890                 895
Lys Tyr Tyr Gly Asn Lys Leu Asn Ala His Leu Asp Ile Thr Asp Asp
            900                 905                 910
Tyr Pro Asn Ser Arg Asn Lys Val Val Lys Leu Ser Leu Lys Pro Tyr
        915                 920                 925
Arg Phe Asp Val Tyr Leu Asp Asn Gly Val Tyr Lys Phe Val Thr Val
930                 935                 940
Lys Asn Leu Asp Val Ile Lys Lys Glu Asn Tyr Tyr Glu Val Asn Ser
945                 950                 955                 960
Lys Cys Tyr Glu Glu Ala Lys Lys Leu Lys Lys Ile Ser Asn Gln Ala
                965                 970                 975
Glu Phe Ile Ala Ser Phe Tyr Asn Asn Asp Leu Ile Lys Ile Asn Gly
            980                 985                 990
Glu Leu Tyr Arg Val Ile Gly Val Asn Asn Asp Leu Leu Asn Arg Ile
        995                 1000                1005
Glu Val Asn Met Ile Asp Ile Thr Tyr Arg Glu Tyr Leu Glu Asn
    1010                1015                1020
Met Asn Asp Lys Arg Pro Pro Arg Ile Ile Lys Thr Ile Ala Ser
    1025                1030                1035
Lys Thr Gln Ser Ile Lys Lys Tyr Ser Thr Asp Ile Leu Gly Asn
    1040                1045                1050
Leu Tyr Glu Val Lys Ser Lys Lys His Pro Gln Ile Ile Lys Lys
    1055                1060                1065
Gly Lys Arg Pro Ala Ala Thr Lys Lys Ala Gly Gln Ala Lys
    1070                1075                1080
```

<210> SEQ ID NO 43
<211> LENGTH: 1158

```
<212> TYPE: PRT
<213> ORGANISM: Artificial Sequence
<220> FEATURE:
<223> OTHER INFORMATION: Synthetic polypeptide

<400> SEQUENCE: 43
```

| | | | | | | | | | | | | | | |
|---|---|---|---|---|---|---|---|---|---|---|---|---|---|---|
| Met | Ala | Pro | Lys | Lys | Arg | Lys | Val | Gly | Ile | His | Gly | Val | Pro | Ala |
| 1 | | | | 5 | | | | | 10 | | | | | 15 |
| Ala | Lys | Arg | Asn | Tyr | Ile | Leu | Gly | Leu | Ala | Ile | Gly | Ile | Thr | Ser | Val |
| | | | 20 | | | | | 25 | | | | | 30 | | |
| Gly | Tyr | Gly | Ile | Ile | Asp | Tyr | Glu | Thr | Arg | Asp | Val | Ile | Asp | Ala | Gly |
| | | 35 | | | | | 40 | | | | | 45 | | | |
| Val | Arg | Leu | Phe | Lys | Glu | Ala | Asn | Val | Glu | Asn | Asn | Glu | Gly | Arg | Arg |
| | 50 | | | | | 55 | | | | | 60 | | | | |
| Ser | Lys | Arg | Gly | Ala | Arg | Arg | Leu | Lys | Arg | Arg | Arg | His | Arg | Ile |
| 65 | | | | 70 | | | | | 75 | | | | | 80 |
| Gln | Arg | Val | Lys | Lys | Leu | Leu | Phe | Asp | Tyr | Asn | Leu | Leu | Thr | Asp | His |
| | | | | 85 | | | | | 90 | | | | | 95 | |
| Ser | Glu | Leu | Ser | Gly | Ile | Asn | Pro | Tyr | Glu | Ala | Arg | Val | Lys | Gly | Leu |
| | | | | 100 | | | | | 105 | | | | | 110 | |
| Ser | Gln | Lys | Leu | Ser | Glu | Glu | Phe | Ser | Ala | Ala | Leu | Leu | His | Leu |
| | | | 115 | | | | | 120 | | | | | 125 | | |
| Ala | Lys | Arg | Arg | Gly | Val | His | Asn | Val | Asn | Glu | Val | Glu | Glu | Asp | Thr |
| 130 | | | | | 135 | | | | | 140 | | | | | |
| Gly | Asn | Glu | Leu | Ser | Thr | Lys | Glu | Gln | Ile | Ser | Arg | Asn | Ser | Lys | Ala |
| 145 | | | | | 150 | | | | | 155 | | | | | 160 |
| Leu | Glu | Glu | Lys | Tyr | Val | Ala | Glu | Leu | Gln | Leu | Glu | Arg | Leu | Lys | Lys |
| | | | | 165 | | | | | 170 | | | | | 175 | |
| Asp | Gly | Glu | Val | Arg | Gly | Ser | Ile | Asn | Arg | Phe | Lys | Thr | Ser | Asp | Tyr |
| | | | 180 | | | | | 185 | | | | | 190 | | |
| Val | Lys | Glu | Ala | Lys | Gln | Leu | Leu | Lys | Val | Gln | Lys | Ala | Tyr | His | Gln |
| | | 195 | | | | | 200 | | | | | 205 | | | |
| Leu | Asp | Gln | Ser | Phe | Ile | Asp | Thr | Tyr | Ile | Asp | Leu | Leu | Glu | Thr | Arg |
| 210 | | | | | 215 | | | | | 220 | | | | | |
| Arg | Thr | Tyr | Tyr | Glu | Gly | Pro | Gly | Glu | Gly | Ser | Pro | Phe | Gly | Trp | Lys |
| 225 | | | | | 230 | | | | | 235 | | | | | 240 |
| Asp | Ile | Lys | Glu | Trp | Tyr | Glu | Met | Leu | Met | Gly | His | Cys | Thr | Tyr | Phe |
| | | | | 245 | | | | | 250 | | | | | 255 | |
| Pro | Glu | Glu | Leu | Arg | Ser | Val | Lys | Tyr | Ala | Tyr | Asn | Ala | Asp | Leu | Tyr |
| | | | 260 | | | | | 265 | | | | | 270 | | |
| Asn | Ala | Leu | Asn | Asp | Leu | Asn | Asn | Leu | Val | Ile | Thr | Arg | Asp | Glu | Asn |
| | | 275 | | | | | 280 | | | | | 285 | | | |
| Glu | Lys | Leu | Glu | Tyr | Tyr | Glu | Lys | Phe | Gln | Ile | Glu | Asn | Val | Phe |
| 290 | | | | | 295 | | | | | 300 | | | | | |
| Lys | Gln | Lys | Lys | Lys | Pro | Thr | Leu | Lys | Gln | Ile | Ala | Lys | Glu | Ile | Leu |
| 305 | | | | | 310 | | | | | 315 | | | | | 320 |
| Val | Asn | Glu | Glu | Asp | Ile | Lys | Gly | Tyr | Arg | Val | Thr | Ser | Thr | Gly | Lys |
| | | | | 325 | | | | | 330 | | | | | 335 | |
| Pro | Glu | Phe | Thr | Asn | Leu | Lys | Val | Tyr | His | Asp | Ile | Lys | Asp | Ile | Thr |
| | | | 340 | | | | | 345 | | | | | 350 | | |
| Ala | Arg | Lys | Glu | Ile | Ile | Glu | Asn | Ala | Glu | Leu | Leu | Asp | Gln | Ile | Ala |
| | | 355 | | | | | 360 | | | | | 365 | | | |
| Lys | Ile | Leu | Thr | Ile | Tyr | Gln | Ser | Ser | Glu | Asp | Ile | Gln | Glu | Glu | Leu |
| 370 | | | | | 375 | | | | | 380 | | | | | |

-continued

```
Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
            405                 410                 415

Asn Leu Ile Leu Asp Glu Leu Trp His Thr Asn Asp Asn Gln Ile Ala
        420                 425                 430

Ile Phe Asn Arg Leu Lys Leu Val Pro Lys Lys Val Asp Leu Ser Gln
    435                 440                 445

Gln Lys Glu Ile Pro Thr Thr Leu Val Asp Asp Phe Ile Leu Ser Pro
        450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Glu Leu Ala Arg
            485                 490                 495

Glu Lys Asn Ser Lys Asp Ala Gln Lys Met Ile Asn Glu Met Gln Lys
                500                 505                 510

Arg Asn Arg Gln Thr Asn Glu Arg Ile Glu Glu Ile Ile Arg Thr Thr
                515                 520                 525

Gly Lys Glu Asn Ala Lys Tyr Leu Ile Glu Lys Ile Lys Leu His Asp
        530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
            580                 585                 590

Gln Glu Glu Ala Ser Lys Lys Gly Asn Arg Thr Pro Phe Gln Tyr Leu
        595                 600                 605

Ser Ser Ser Asp Ser Lys Ile Ser Tyr Glu Thr Phe Lys Lys His Ile
        610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
            645                 650                 655

Phe Ile Asn Arg Asn Leu Val Asp Thr Arg Tyr Ala Thr Arg Gly Leu
            660                 665                 670

Met Asn Leu Leu Arg Ser Tyr Phe Arg Val Asn Asn Leu Asp Val Lys
        675                 680                 685

Val Lys Ser Ile Asn Gly Gly Phe Thr Ser Phe Leu Arg Arg Lys Trp
690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
            725                 730                 735

Leu Asp Lys Ala Lys Lys Val Met Glu Asn Gln Met Phe Glu Glu Lys
        740                 745                 750

Gln Ala Glu Ser Met Pro Glu Ile Glu Thr Glu Gln Glu Tyr Lys Glu
        755                 760                 765

Ile Phe Ile Thr Pro His Gln Ile Lys His Ile Lys Asp Phe Lys Asp
        770                 775                 780

Tyr Lys Tyr Ser His Arg Val Asp Lys Lys Pro Asn Arg Glu Leu Ile
785                 790                 795                 800

Asn Asp Thr Leu Tyr Ser Thr Arg Lys Asp Asp Lys Gly Asn Thr Leu
```

```
                    805                 810                 815
Ile Val Asn Asn Leu Asn Gly Leu Tyr Asp Lys Asp Asn Asp Lys Leu
                820                 825                 830

Lys Lys Leu Ile Asn Lys Ser Pro Glu Lys Leu Leu Met Tyr His His
            835                 840                 845

Asp Pro Gln Thr Tyr Gln Leu Lys Leu Ile Met Glu Gln Tyr Gly
        850                 855                 860

Asp Glu Lys Asn Pro Leu Tyr Lys Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
            900                 905                 910

Tyr Pro Asn Ser Arg Asn Lys Val Val Lys Leu Ser Leu Lys Pro Tyr
        915                 920                 925

Arg Phe Asp Val Tyr Leu Asp Asn Gly Val Tyr Lys Phe Val Thr Val
930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
            980                 985                 990

Glu Leu Tyr Arg Val Ile Gly Val Asn Asn Asp Leu Leu Asn Arg Ile
        995                 1000                1005

Glu Val Asn Met Ile Asp Ile Thr Tyr Arg Glu Tyr Leu Glu Asn
        1010                1015                1020

Met Asn Asp Lys Arg Pro Pro Arg Ile Ile Lys Thr Ile Ala Ser
        1025                1030                1035

Lys Thr Gln Ser Ile Lys Lys Tyr Ser Thr Asp Ile Leu Gly Asn
        1040                1045                1050

Leu Tyr Glu Val Lys Ser Lys Lys His Pro Gln Ile Ile Lys Lys
        1055                1060                1065

Gly Lys Arg Pro Ala Ala Thr Lys Lys Ala Gly Gln Ala Lys Lys
        1070                1075                1080

Lys Lys Gly Ser Asp Ala Lys Ser Leu Thr Ala Trp Ser Arg Thr
        1085                1090                1095

Leu Val Thr Phe Lys Asp Val Phe Val Asp Phe Thr Arg Glu Glu
        1100                1105                1110

Trp Lys Leu Leu Asp Thr Ala Gln Gln Ile Val Tyr Arg Asn Val
        1115                1120                1125

Met Leu Glu Asn Tyr Lys Asn Leu Val Ser Leu Gly Tyr Gln Leu
        1130                1135                1140

Thr Lys Pro Asp Val Ile Leu Arg Leu Glu Lys Gly Glu Glu Pro
        1145                1150                1155

<210> SEQ ID NO 44
<211> LENGTH: 1483
<212> TYPE: PRT
<213> ORGANISM: Artificial Sequence
<220> FEATURE:
<223> OTHER INFORMATION: Synthetic polypeptide

<400> SEQUENCE: 44

Met Asp Lys Lys Tyr Ser Ile Gly Leu Ala Ile Gly Thr Asn Ser Val
```

-continued

```
1               5                    10                   15
Gly Trp Ala Val Ile Thr Asp Glu Tyr Lys Val Pro Ser Lys Lys Phe
                20                  25                  30
Lys Val Leu Gly Asn Thr Asp Arg His Ser Ile Lys Lys Asn Leu Ile
                35                  40                  45
Gly Ala Leu Leu Phe Asp Ser Gly Glu Thr Ala Glu Ala Thr Arg Leu
                50                  55                  60
Lys Arg Thr Ala Arg Arg Arg Tyr Thr Arg Arg Lys Asn Arg Ile Cys
 65             70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
```

```
Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845
```

```
Asp Asp Ser Ile Asp Asn Lys Val Leu Thr Arg Ser Asp Lys Asn Arg
    850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
```

```
                 1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Thr Gly Gly Pro Lys Lys Lys Arg Lys Val Tyr Pro Tyr Asp
    1370                1375                1380

Val Pro Asp Tyr Ala Gly Tyr Pro Tyr Asp Val Pro Asp Tyr Ala
    1385                1390                1395

Gly Ser Tyr Pro Tyr Asp Val Pro Asp Tyr Ala Gly Ser Met Asp
    1400                1405                1410

Ala Lys Ser Leu Thr Ala Trp Ser Arg Thr Leu Val Thr Phe Lys
    1415                1420                1425

Asp Val Phe Val Asp Phe Thr Arg Glu Glu Trp Lys Leu Leu Asp
    1430                1435                1440

Thr Ala Gln Gln Ile Val Tyr Arg Asn Val Met Leu Glu Asn Tyr
    1445                1450                1455

Lys Asn Leu Val Ser Leu Gly Tyr Gln Leu Thr Lys Pro Asp Val
    1460                1465                1470

Ile Leu Arg Leu Glu Lys Gly Glu Glu Pro
    1475                1480

<210> SEQ ID NO 45
<211> LENGTH: 1069
<212> TYPE: PRT
<213> ORGANISM: Artificial Sequence
<220> FEATURE:
<223> OTHER INFORMATION: Synthetic polypeptide

<400> SEQUENCE: 45

Met Ala Pro Lys Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
                20                  25                  30

Gly Tyr Gly Ile Ile Asp Tyr Glu Thr Arg Asp Val Ile Asp Ala Gly
            35                  40                  45

Val Arg Leu Phe Lys Glu Ala Asn Val Glu Asn Asn Glu Gly Arg Arg
        50                  55                  60

Ser Lys Arg Gly Ala Arg Arg Leu Lys Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Glu Phe Ser Ala Ala Leu Leu His Leu
```

```
            115                 120                 125
Ala Lys Arg Arg Gly Val His Asn Val Asn Glu Val Glu Glu Asp Thr
        130                 135                 140
Gly Asn Glu Leu Ser Thr Lys Glu Gln Ile Ser Arg Asn Ser Lys Ala
145                 150                 155                 160
Leu Glu Glu Lys Tyr Val Ala Glu Leu Gln Leu Glu Arg Leu Lys Lys
                165                 170                 175
Asp Gly Glu Val Arg Gly Ser Ile Asn Arg Phe Lys Thr Ser Asp Tyr
            180                 185                 190
Val Lys Glu Ala Lys Gln Leu Leu Lys Val Gln Lys Ala Tyr His Gln
        195                 200                 205
Leu Asp Gln Ser Phe Ile Asp Thr Tyr Ile Asp Leu Leu Glu Thr Arg
210                 215                 220
Arg Thr Tyr Tyr Glu Gly Pro Gly Glu Gly Ser Pro Phe Gly Trp Lys
225                 230                 235                 240
Asp Ile Lys Glu Trp Tyr Glu Met Leu Met Gly His Cys Thr Tyr Phe
                245                 250                 255
Pro Glu Glu Leu Arg Ser Val Lys Tyr Ala Tyr Asn Ala Asp Leu Tyr
            260                 265                 270
Asn Ala Leu Asn Asp Leu Asn Asn Leu Val Ile Thr Arg Asp Glu Asn
        275                 280                 285
Glu Lys Leu Glu Tyr Tyr Glu Lys Phe Gln Ile Ile Glu Asn Val Phe
290                 295                 300
Lys Gln Lys Lys Lys Pro Thr Leu Lys Gln Ile Ala Lys Glu Ile Leu
305                 310                 315                 320
Val Asn Glu Glu Asp Ile Lys Gly Tyr Arg Val Thr Ser Thr Gly Lys
                325                 330                 335
Pro Glu Phe Thr Asn Leu Lys Val Tyr His Asp Ile Lys Asp Ile Thr
            340                 345                 350
Ala Arg Lys Glu Ile Ile Glu Asn Ala Glu Leu Leu Asp Gln Ile Ala
        355                 360                 365
Lys Ile Leu Thr Ile Tyr Gln Ser Ser Glu Asp Ile Gln Glu Glu Leu
370                 375                 380
Thr Asn Leu Asn Ser Glu Leu Thr Gln Glu Glu Ile Glu Gln Ile Ser
385                 390                 395                 400
Asn Leu Lys Gly Tyr Thr Gly Thr His Asn Leu Ser Leu Lys Ala Ile
                405                 410                 415
Asn Leu Ile Leu Asp Glu Leu Trp His Thr Asn Asp Asn Gln Ile Ala
            420                 425                 430
Ile Phe Asn Arg Leu Lys Leu Val Pro Lys Lys Val Asp Leu Ser Gln
        435                 440                 445
Gln Lys Glu Ile Pro Thr Thr Leu Val Asp Asp Phe Ile Leu Ser Pro
450                 455                 460
Val Val Lys Arg Ser Phe Ile Gln Ser Ile Lys Val Ile Asn Ala Ile
465                 470                 475                 480
Ile Lys Lys Tyr Gly Leu Pro Asn Asp Ile Ile Ile Glu Leu Ala Arg
                485                 490                 495
Glu Lys Asn Ser Lys Asp Ala Gln Lys Met Ile Asn Glu Met Gln Lys
            500                 505                 510
Arg Asn Arg Gln Thr Asn Glu Arg Ile Glu Glu Ile Ile Arg Thr Thr
        515                 520                 525
Gly Lys Glu Asn Ala Lys Tyr Leu Ile Glu Lys Ile Lys Leu His Asp
530                 535                 540
```

```
Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
            565                 570                 575

Arg Ser Val Ser Phe Asp Asn Ser Phe Asn Asn Lys Val Leu Val Lys
            580                 585                 590

Gln Glu Glu Ala Ser Lys Lys Gly Asn Arg Thr Pro Phe Gln Tyr Leu
            595                 600                 605

Ser Ser Ser Asp Ser Lys Ile Ser Tyr Glu Thr Phe Lys Lys His Ile
        610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
            660                 665                 670

Met Asn Leu Leu Arg Ser Tyr Phe Arg Val Asn Asn Leu Asp Val Lys
        675                 680                 685

Val Lys Ser Ile Asn Gly Gly Phe Thr Ser Phe Leu Arg Arg Lys Trp
690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
            740                 745                 750

Gln Ala Glu Ser Met Pro Glu Ile Glu Thr Glu Gln Glu Tyr Lys Glu
        755                 760                 765

Ile Phe Ile Thr Pro His Gln Ile Lys His Ile Lys Asp Phe Lys Asp
770                 775                 780

Tyr Lys Tyr Ser His Arg Val Asp Lys Lys Pro Asn Arg Glu Leu Ile
785                 790                 795                 800

Asn Asp Thr Leu Tyr Ser Thr Arg Lys Asp Asp Lys Gly Asn Thr Leu
                805                 810                 815

Ile Val Asn Asn Leu Asn Gly Leu Tyr Asp Lys Asp Asn Asp Lys Leu
            820                 825                 830

Lys Lys Leu Ile Asn Lys Ser Pro Glu Lys Leu Leu Met Tyr His His
        835                 840                 845

Asp Pro Gln Thr Tyr Gln Lys Leu Lys Leu Ile Met Glu Gln Tyr Gly
        850                 855                 860

Asp Glu Lys Asn Pro Leu Tyr Lys Tyr Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
                900                 905                 910

Tyr Pro Asn Ser Arg Asn Lys Val Val Lys Leu Ser Leu Lys Pro Tyr
            915                 920                 925

Arg Phe Asp Val Tyr Leu Asp Asn Gly Val Tyr Lys Phe Val Thr Val
            930                 935                 940

Lys Asn Leu Asp Val Ile Lys Lys Glu Asn Tyr Tyr Glu Val Asn Ser
945                 950                 955                 960
```

-continued

```
Lys Cys Tyr Glu Glu Ala Lys Lys Leu Lys Lys Ile Ser Asn Gln Ala
                965             970                 975

Glu Phe Ile Ala Ser Phe Tyr Asn Asn Asp Leu Ile Lys Ile Asn Gly
            980             985                 990

Glu Leu Tyr Arg Val Ile Gly Val  Asn Asn Asp Leu Leu  Asn Arg Ile
        995             1000                 1005

Glu Val  Asn Met Ile Asp Ile  Thr Tyr Arg Glu Tyr  Leu Glu Asn
    1010             1015                 1020

Met Asn Asp Lys Arg Pro Pro  Arg Ile Ile Lys Thr  Ile Ala Ser
    1025             1030                 1035

Lys Thr Gln Ser Ile Lys Lys  Tyr Ser Thr Asp Ile  Leu Gly Asn
    1040             1045                 1050

Leu Tyr Glu Val Lys Ser Lys  Lys His Pro Gln Ile  Ile Lys Lys
    1055             1060                 1065

Gly
```